US007485428B2

(12) United States Patent
Armes et al.

(10) Patent No.: US 7,485,428 B2
(45) Date of Patent: Feb. 3, 2009

(54) RECOMBINASE POLYMERASE AMPLIFICATION

(75) Inventors: Niall A. Armes, Fulbourn (GB); Derek L. Stemple, St. Albans (GB)

(73) Assignee: TwistDx, Inc., Cambridge, MA (US)

( * ) Notice: Subject to any disclaimer, the term of this patent is extended or adjusted under 35 U.S.C. 154(b) by 0 days.

(21) Appl. No.: 11/893,113

(22) Filed: Aug. 13, 2007

(65) Prior Publication Data

US 2008/0076160 A1    Mar. 27, 2008

Related U.S. Application Data

(63) Continuation of application No. 10/371,641, filed on Feb. 21, 2003, now Pat. No. 7,270,981.

(60) Provisional application No. 60/358,563, filed on Feb. 21, 2002.

(51) Int. Cl.
*C12Q 1/68* (2006.01)
*C12P 19/34* (2006.01)

(52) U.S. Cl. .......................... 435/6; 435/91.1; 435/91.2

(58) Field of Classification Search ..................... 435/6, 435/91.1, 91.2
See application file for complete search history.

(56) References Cited

U.S. PATENT DOCUMENTS

| 4,683,195 | A | 7/1987 | Mulis et al. |
|---|---|---|---|
| 4,965,188 | A | 10/1990 | Mulis et al. |
| 5,223,414 | A | 6/1993 | Zarling et al. |
| 5,273,881 | A | 12/1993 | Sena et al. |
| 5,670,316 | A | 9/1997 | Sena et al. |
| 6,087,112 | A * | 7/2000 | Dale .............................. 435/6 |
| 6,929,915 | B2 | 8/2005 | Benkovic et al. |
| 2003/0108936 | A1 | 6/2003 | Wagner |
| 2004/0224336 | A1 | 11/2004 | Wagner |
| 2005/0112631 | A1 | 5/2005 | Piepenberg |
| 2005/0136443 | A1 | 6/2005 | Shigemon |

FOREIGN PATENT DOCUMENTS

| WO | 98/08975 | 3/1998 |
|---|---|---|
| WO | WO 02/086167 | 10/2002 |

OTHER PUBLICATIONS

Adams et al. (1994). *Proc. Natl. Acad. Sci. USA* 91: 9901-9905.
Alexseyev et al. (1996). *J. Bacteriology* 178: 2018-2024.
Bains and Smith (1988). *J. Theor. Biol.* 135: 303-307.
Baumann et al. (1997). *Mutat Res* 384: 65-72.
Benkovic et al. (2001). *Annu. Rev. Biochem.* 70: 181-208.
Bennett and Holloman (2001). *Biochem.* 40: 2942-2953.
Better and Helinski (1983). *J. Bacteriology* 155: 311-316.
Bork et al. (2001). *EMBO J.* 20: 7313-7322.
Bork et al. (2001). *J. Biol. Chem.* 276: 45740-45743.
Compton (1991). *Nature* 350: 91-92.
Cox et al. (2000). *Nature* 404: 37-41.
Cox et al. (1981). *J. Biol.Chem.* 256: 4676-4678.
Cromie and Leach (2000). *Mol. Cell.* 6: 815-826.
Dmanac et al. (1989). *Genomics* 4: 114-128.
Dillingham and Kowalczykowski (2001). *Mol. Cell.* 8: 734-736.
Eggler et al. (2003). *J. Boil. Chem.* 278: 16389-16396.
Eggleston and West (2000). *J. Biol. Chem.* 275: 26467-26476.
Elias-Arnanz and Salas (1997). *EMBO J.* 16: 5775-5783.
Ferrari et al. (1994). *J. Mol. Biol.* 236: 106-123.
Formosa et al. (1983). *Proc. Natl. Acad. Sci. USA* 80: 2442-2446.
Formosa and Alberts (1986). *J. Biol. Chem.* 261: 6107-6118.
Formosa and Alberts (1986). *Cell* 47: 793-806.
Glover and McHenry (2001). *Cell* 105: 925-934.
Goodman et al. (1987). *Gene* 58: 265-271.
Hacker and Alberts (1992). *J. Biol. Chem.* 267: 20674-20681.
Harris and Griffith (1989). *J. Mol. Biol.* 206: 19-27.
Harris and Griffith (1987). *J. Biol. Chem.* 262: 9285-9292.
Heyer and Kolodner (1989). *Biochemistry* 28: 2856-2862.
Hickson et al. (1981). *Mol. Gen. Genet.* 184: 68-72.
Hsieh et al. (1992). *Proc. Natl. Acad. Sci. USA* 89: 6492-6496.
Kato and Kuramitsu (1993). *J. Biochem.* (Toyko) 114: 926-929.
Katz and Bryant (2001). *Biochemistry* 40: 11082-11089.
Kelman and O'Donnell (1995). *Annu. Rev. Biochem.* 64: 171-200.
Khrapko et al. (1989). *FEBS Lett.* 256: 118-122.
Komori et al. (2000). *J. Biol. Chem.* 275: 33782-33790.
Kowalczykowski et al. (1987). *J. Mol. Biol.* 193: 81-95.
Kuil et al. (1988). *Biophys. Chem.* 32: 211-227.
Kuramitsu et al. (1981). *J. Biochem.* (Tokyo) 90: 1033-1045.
Kurumizaka et al. (1994). *J. Biol. Chem.* 269: 3068-3075.
Lavery and Kowalczykowski (1992). *J. Biol. Chem.* 267: 9307-9314.
Liu et al. (1996). *J. Biol. Chem.* 271: 15656-15661.
Lohman and Ferrari (1994). *Annu. Rev. Biochem.* 63: 527-570.
Lovett and Roberts (1985). *J. Biol. Chem.* 260: 3305-3313.
Lysov et al. (1988). *SSSR* 303: 1508-1511.
Maeshima et al. (1996). *Genes Cells* 1: 1057-1068.
Marians (1992). *Annu. Rev. Biochem.* 61: 673-719.
Marians (1999). *Prog. Nucl. Acid Res. Mol. Biol.* 63: 39-67.
Mazin and Kowalczykowski (1998). *EMBO J.* 17: 1161-1168.
Maxam and Gilbert (1977). *Proc. Natl. Acad. Sci. USA* 74: 560-564.
McGlynn and Lloyd (1999). *Nuc. Acids Res.* 27: 3049-3056.
McGlynn et al. (2000). *Nuc. Acids Res.* 28: 2324-2332.
Morel et al. (1997). *J. Biol. Chem.* 272: 17091-17096.
Morrical et al. (1991). *J. Biol. Chem.* 266: 14031-14038.
Morrical and Alberts (1990). *J. Biol. Chem.* 265: 15096-15103.
Ng and Marians (1996). *J. Biol. Chem.* 271: 15642-15648.
Ng and Marians (1996). *J. Biol. Chem.* 271: 15649-15655.
Paulus and Bryant (1997). *Biochemistry* 36: 7832-7838.
Pevzner (1989). *J. Biomol. Struct. Dyn.* 7: 63-73.

(Continued)

*Primary Examiner*—Kenneth R. Horlick
(74) *Attorney, Agent, or Firm*—Mintz, Levin, Cohn, Ferris, Glovsky & Popeo, P.C.

(57) ABSTRACT

This disclosure describe three related novel methods for Recombinase-Polymerase Amplification (RPA) of a target DNA that exploit the properties of the bacterial RecA and related proteins, to invade double-stranded DNA with single stranded homologous DNA permitting sequence specific priming of DNA polymerase reactions. The disclosed methods has the advantage of not requiring thermocycling or thermophilic enzymes. Further, the improved processivity of the disclosed methods allow amplification of DNA up to hundreds of megabases in length.

12 Claims, 12 Drawing Sheets

OTHER PUBLICATIONS

Pham et al. (2001). *Nature* 409: 366-370.
Pierre and Paoletti (1983). *J. Biol. Chem.* 258: 2870-2874.
Rashid et al. (2001). *Methods in Enzymol.* 334: 261-270.
Reddy et al. (1993). *Proc. Natl. Acad. Sci. USA* 90: 3211-3215.
Riddles and Lehman (1985). *J. Biol. Chem.* 260: 170-173.
Ronaghi et al. (1998). *Science* 281: 363-365.
Rosselli and Stasiak (1990). *J. Mol. Biol.* 216: 335-352.
Saiki et al. (1988). *Science* 239: 487-491.
Salinas et al. (1995). *J. Biol. Chem.* 270: 5181-5186.
Sanger et al. (1977). *Proc. Natl. Acad. Sci. USA* 75: 5463-5467.
Scheerhagen et al. (1986). *J. Biomol. Struct. Dyn.* 3: 887-898.
Shan et al. (1997). *J. Mol. Bio.* 265: 519-540.
Shibata (1979). *Proc. Natl. Acad. Sci. USA* 76: 1638-1642.
Shibata et al. (1980). *Proc. Natl. Acad. Sci. USA* 77: 2606-2610.
Singleton et al. (2001). *Cell* 107: 79-89.
Southern et al. (1992). *Genomics* 13: 1008-1017.
Spies et al. (2000). *Eur. J. Biochem.* 267: 1125-1137.
Steffen and Bryant (2000). *Arch. Biochem. and Biophys.* 382: 303-309.
Tang et al. (2000). *Nature* 404: 1014-1018.
Tissier et al. (1995). *Plant Physiol.* 108: 379-386.
Voloshin et al. (1996). *Science* 272: 868-872.
Villemain et al. (2000). *J. Biol. Chem.* 275: 31496-31504.
Walker et al. (1992). *Proc. Natl. Acad. Sci. USA* 89: 392-396.
Webb et al. (1995). *J. Biol. Chem.* 270: 31397-31404.
Webb et al. (1997). *Cell* 91: 347-356.
Webb et al. (1999). *J. Biol. Chem.* 274: 15367-15374.
West et al. (1983). *J. Biol. Chem.* 258: 4648-4654.
Wetmur et al. (1994). *J. Biol. Chem.* 269: 25928-25935.
Xu and Marians (2002). *J. Biol. Chem.* 277: 14321-14328.
Yonesaki et al. (1985). *Eur. J. Biochem.* 148: 127-134.
Zhang et al. (2001). *Mol. Diagn.* 6: 141-150.
Partial European Search Report for EP 08 01 2222, 3 pgs., mailed Nov. 12, 2008.
Bianco, P R et al. (1998) *Frontiers in Bioscience* 3 D570-D603.
Piepenburg, O et al. (2006) *PLOS Biology* 4 (7) 204.
Salinas, F et al. (2000). *Proc. Natl. Acad. Sci. USA* 97 (13) 7196-7201.

* cited by examiner

Target A Oligonucleotide ———
Target B Oligonucleotide ———
RecA ∿∿∿
SSB ⬭
RecO, RecR ◉

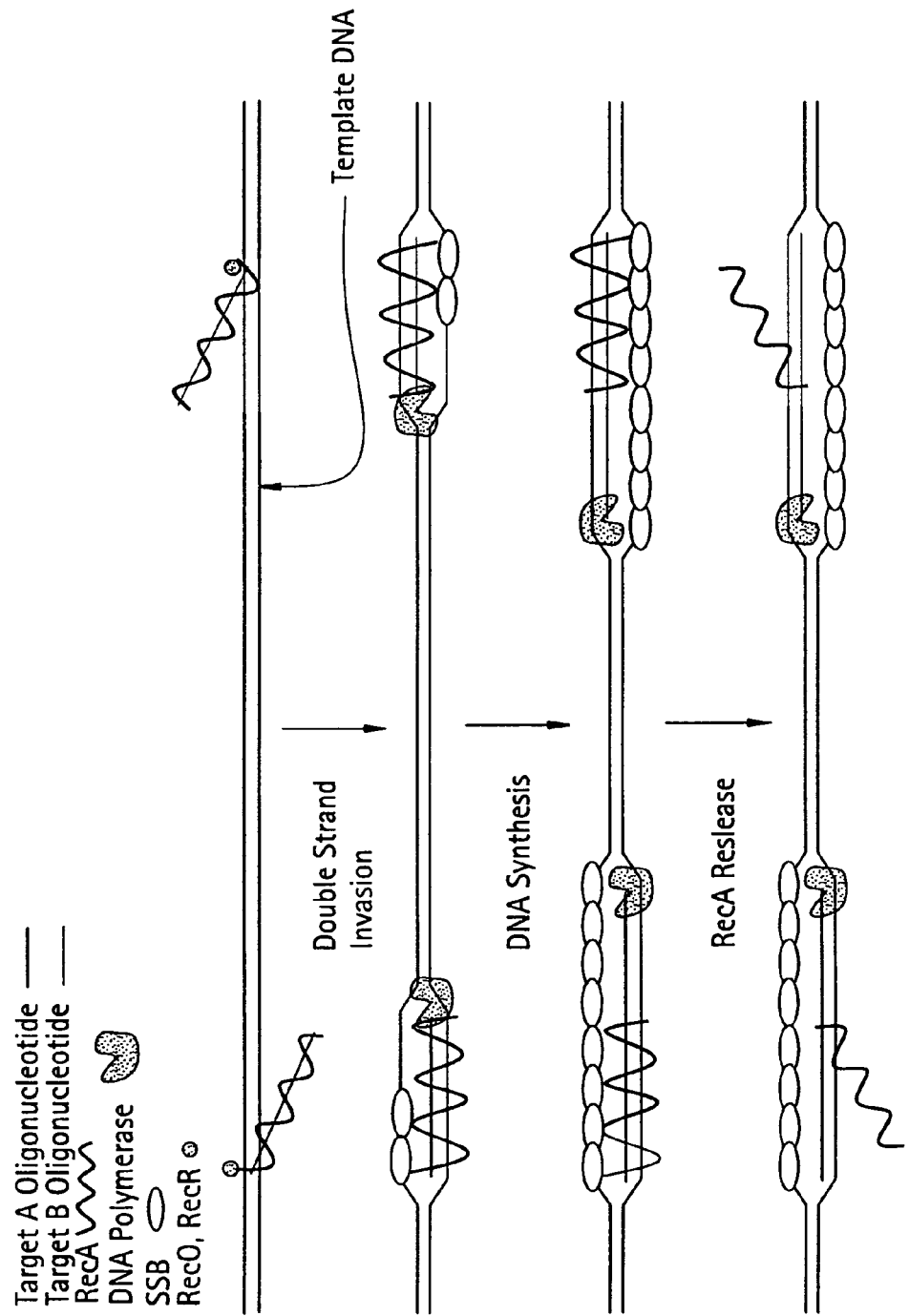

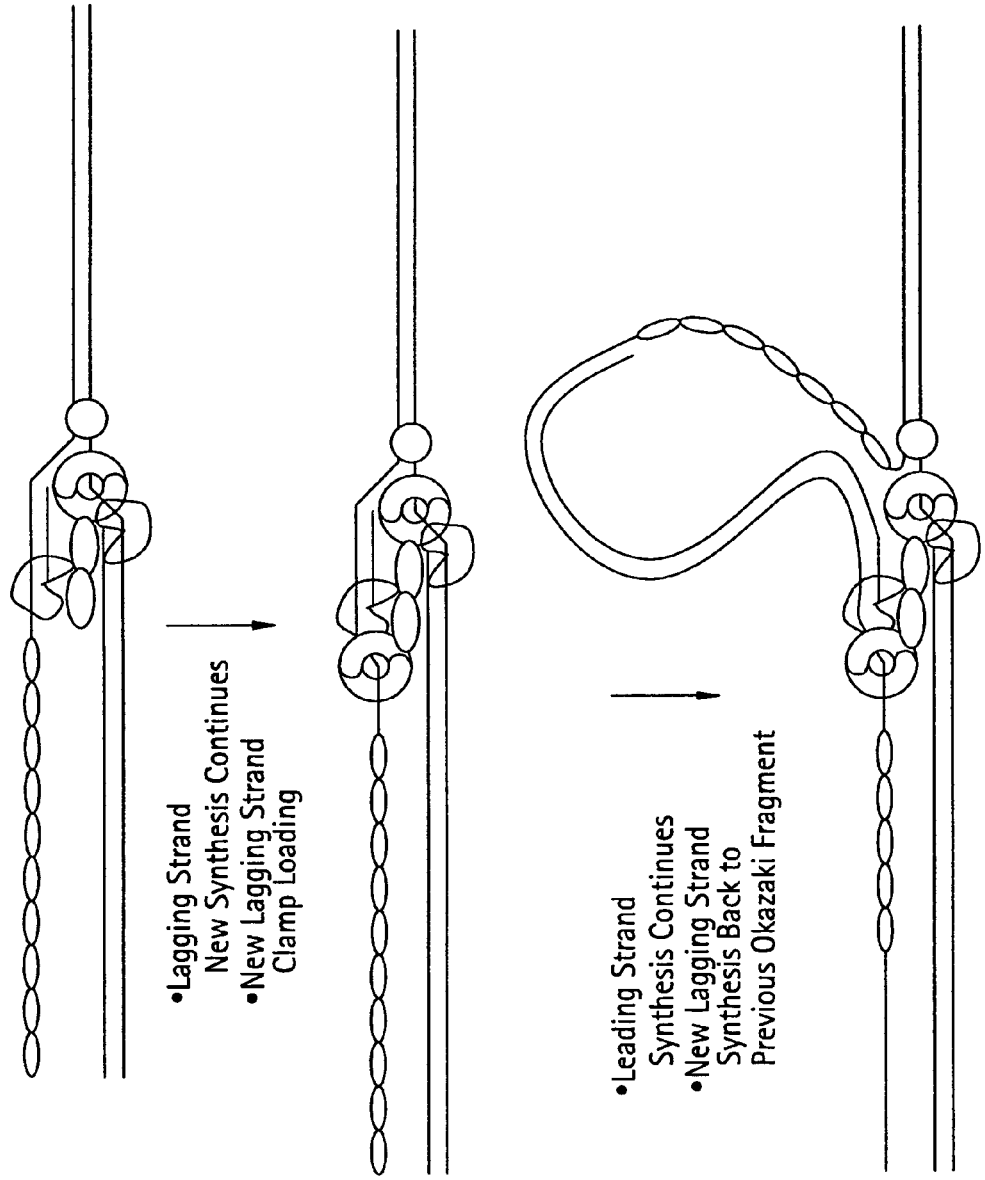

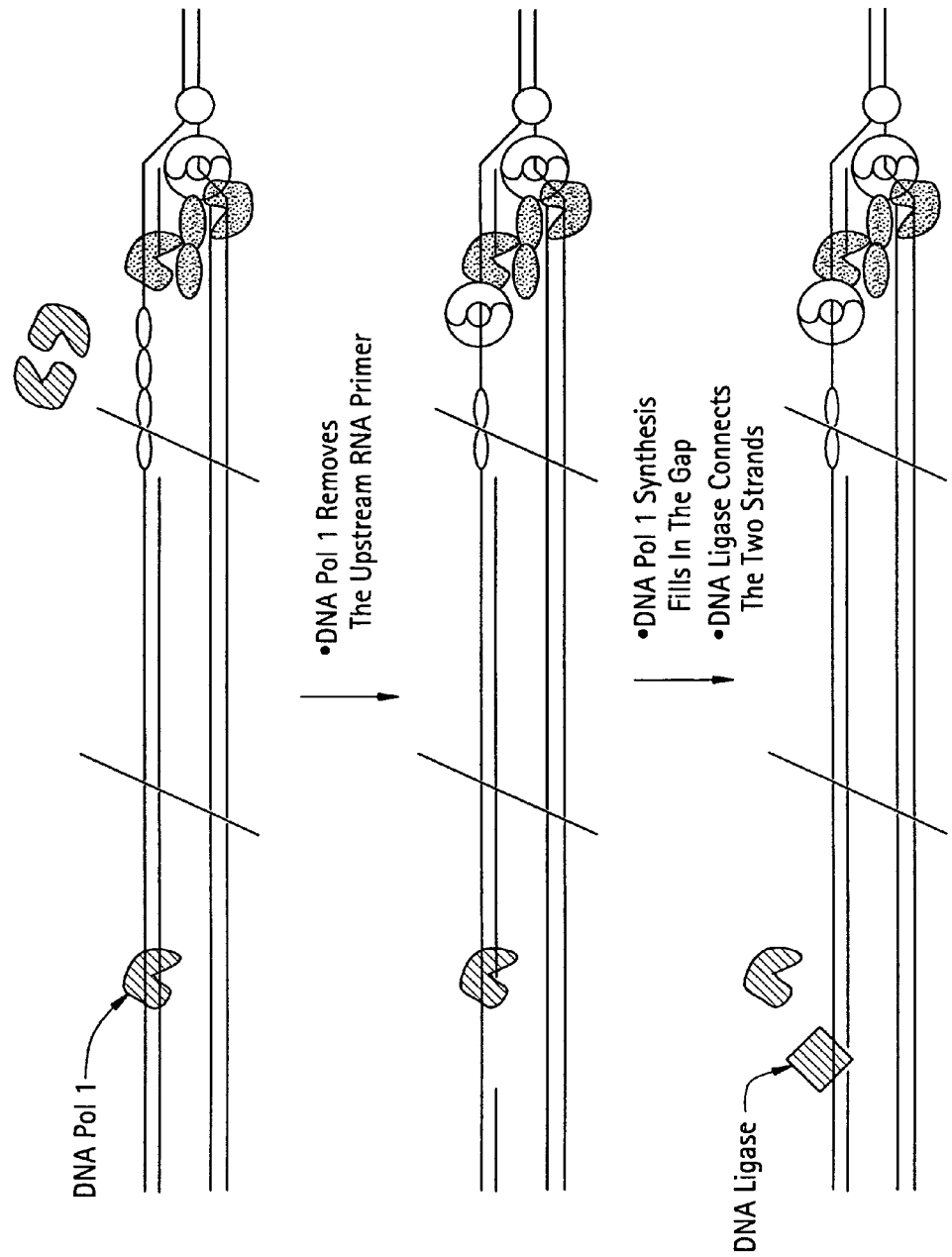

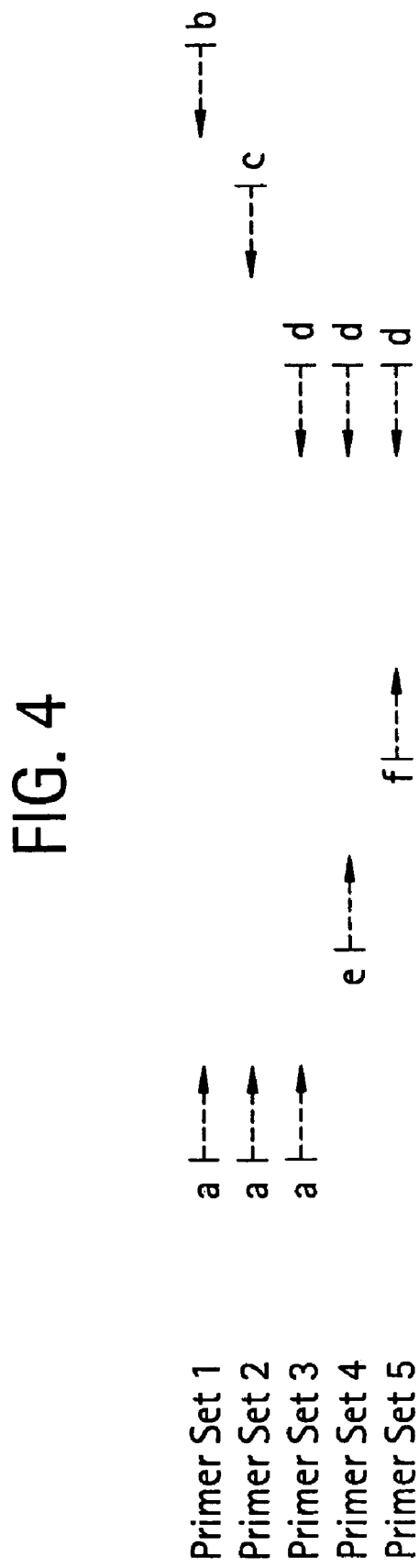

Examples of suitable double stranded template nucleic acids.

Orientation of nucleic acid primer pairs.

RPA Reaction in Progress

RECOMBINASE POLYMERASE AMPLIFICATION

RELATED APPLICATIONS

This application is a continuation of U.S. Ser. No. 10/371,641, filed Feb. 21, 2003, which is now U.S. Pat. No. 7,270,981. U.S. Ser. No. 10/371,641 is incorporated herein in its entirety. This application claims the benefit of priority to U.S. Ser. No. 60/358,563 filed Feb. 21, 2002. U.S. Ser. No. 60/358,563 is incorporated herein in its entirety.

BACKGROUND

Throughout this specification, various patents, published patent applications and scientific references are cited to describe the state and content of the art. Those disclosures, in their entireties, are hereby incorporated into the present specification by reference.

The ability to amplify DNA lies at the heart of modern biological and medical research. This is because most molecular biology techniques rely on samples containing many identical molecules to increase the sensitivity of an assay or to prepare enough material for further processing. Among the various nucleic acid amplification techniques, polymerase chain reaction (PCR) is the most common because of its sensitivity and efficiency at amplifying short nucleic acid sequences.

While PCR is of great utility, it is also limited in a number of ways. The first limitation of PCR is that it relies on multiple cycles of thermal melting (denaturing) at high temperatures followed by hybridization and elongation at a reduced temperature. To maximize efficiency and to minimize noise, complex temperature control of multiple reactions is required. This necessitates the use of a thermocycler controllable rapid heating/cooling block made with exotic material (e.g., gold plated silver blocks), or a robotic mechanism to move samples between temperature-controlled zones. Because of the high-temperature required to melt DNA in physiological salt conditions, PCR technology requires either the addition of fresh polymerase per cycle or the use of thermostable polymerases. The approach of adding fresh polymerase has not been automated and is thus labor intensive and prone to errors (e.g., contamination, dropped tubes, labeling errors). Furthermore, the need to add enzymes and to mix each reaction individually presents serious drawbacks that have limited adaptation of enzyme-addition PCR methods to the small scale.

Compared to methods involving the addition of fresh polymerase, the use of thermostable polymerases in PCR is the most widely practiced. This approach suffers from the fact that thermostable polymerases are found in a limited number of organisms, and the replication mechanisms used by thermophilic organisms are poorly understood. The available repertoire of thermostable polymerases is limited to single polypeptide polymerase enzymes involved in DNA repair, and/or lagging strand synthesis. DNA repair and/or lagging strand polymerases are poor choices for DNA amplification because they exhibit poor processivity (distributive synthesis). In part as a consequence of using repair and/or lagging strand polymerases (e.g. Taq, Pfu, Vent polymerases), and due to the formation of inhibitory secondary or tertiary nucleic acid structures following thermal melting, current PCR protocols do not readily amplify sequences longer than several thousands of base pairs. Reliable synthesis (and amplification) of longer templates will rely on polymerases and auxiliary enzymatic complexes collectively exhibiting much higher levels of processivity, strand displacement, and secondary structure resolution, as well as limiting the formation of inhibitory higher order nucleic acid structures which may form on cooling heat-denatured DNA.

A second limitation of PCR is that it relies on solution hybridization between oligonucleotides (PCR primers) and denatured template DNA (i.e., the DNA to be amplified) in an aqueous environment. To be effective, PCR reactions are performed in a short time because the thermostable polymerases have a rapidly declining activity at PCR temperatures. Further, for effective hybridization in a short time, a feature critical to rapid turnaround, it is necessary to perform PCR in an environment with high concentrations of oligonucleotides. The high oligonucleotide concentration also ensures rapid interaction of target sequences with the oligonucleotides in competition with the heat-denatured complementary strand still present in solution. High oligonucleotide primer concentrations can cause problems, particularly when the copy number of the target sequence is low and present in a complex mixture of DNA molecules. This would be the case, for example, in a PCR of a genome to determine the genetic polymorphism in one locus.

One problem with using high oligonucleotide concentrations is that it enhances the degree of false priming at only partly matched sequences in the complex DNA mixture. False priming refers to the hybridization of a primer to a template DNA in PCR even when the primer sequence is not completely complementary to the template nucleic acid, which can lead to non-specific amplification of nucleic acids. Noise, due to false priming, increases with the oligonucleotide concentration and the complexity of total starting DNA. In addition, the possibility of false priming increases as the copy number of target sequences decreases. Where the conditions for false priming are favorable (i.e., high oligonucleotide concentration, high complexity, low copy number), errant amplified sequences can become a dominant reaction product. Consequently it can be difficult to identify conditions, and oligonucleotides, for clean amplification of target sequences from a sample DNA without an excess of false priming background. Thus a further disadvantage of using PCR is the limited success at cleanly amplifying rare target DNAs from complex sequences mixtures.

One solution to the problems of specificity and template-melting problem incurred by PCR is to employ methods that rely on the biological properties of the bacterial RecA protein, or its prokaryotic and eukaryotic relatives. These proteins coat single-stranded DNA (ssDNA) to form filaments, which then scan double-stranded DNA (dsDNA) for regions of sequence homology. When homologous sequences are located, the nucleoprotein filament strand invades the dsDNA creating a short hybrid and a displaced strand bubble known as a D-loop. The free 3'-end of the filament strand in the D-loop can be extended by DNA polymerases to synthesize a new complementary strand. The complementary strand displaces the originally paired strand as it elongates. By utilizing pairs of oligonucleotides in a manner similar to that used in PCR it should be possible to amplify target DNA sequences in an analogous fashion but without any requirement for thermal melting (thermocycling). This has the advantage both of allowing the use of heat labile polymerases previously unusable in PCR, and increasing the fidelity and sensitivity by template scanning and strand invasion instead of hybridization.

Although the use of RecA and its homologues for in vitro amplification of nucleic acids has been previously described (U.S. Pat. No. 5,223,414 to Zarling et al., referred to herein as "Zarling"), the method and results are limited. Zarling's method have critical failings, which have limited its ability to achieve exponential amplification of double-stranded DNA. The failure of the Zarling method to achieve exponential amplification may be due to its specification for the use of ATPγS rather than ATP. The Zarling method urges the use of ATPγS, instead of ATP, in the assembly of RecA nucleoprotein filaments because it results in a more stable RecA/ssDNA filament structure. Normally, filaments are assembled in a 5' to 3' direction and will spontaneously disassemble in the same 5' to 3' direction as RecA hydrolyzes ATP. This process is dynamic in that assembly and disassembly occurs at the same time and the amount of assembled filaments is at equilibrium. If the non-hydrolyzable ATP analog, ATPγS, is used, hydrolysis of the ATPγS and the 5' to 3' disassembly of the filaments are inhibited. The great stability of RecA/ATPγS filaments, both before and after strand exchange, while helpful in the method of targeting (i.e., the Zarling method) is detrimental and unpractical for DNA amplification.

In the Zarling method, RecA protein involved in strand invasion will remain associated with the double-stranded portion of the exchanged material after strand exchange. This interaction occurs because the newly formed duplex is bound in the high-affinity site of RecA. The displaced strand occupies a different low-affinity site, unless it is bound to another single-stranded DNA binding protein (SSB), such as E. coli SSB. If ATP had been utilized to generate the exchange structure, spontaneous 5' to 3' disassembly might occur, although the exchange complex can be quite stable and may require additional factors to stimulate ATP-dependent disassembly. Regardless of whether spontaneous or stimulated, in the presence of ATPγS, 5' to 3' disassembly of the RecA filament is inhibited (Paulus, B. F. and Bryant, F. R. (1997). Biochemistry 36, 7832-8; Rosselli, W. and Stasiak, A. (1990). J Mol Biol 216, 335-52; Shan, Q. et al., (1997). J Mol Biol 265, 519-40). These RecA/dsDNA complexes are precisely the sites targeted by the RecA/ssDNA primer complexes used to initiate subsequent rounds of invasion and synthesis. With the RecA bound, the dsDNAs can no longer be invaded by RecA/ssDNA primer complexes and are therefore not amplifiable from this point. Further synthesis from these templates might occur if initiated at the other end of the template, which is free of RecA, and this might eventually lead to displacement of the bound RecA. It is not clear, however, whether many polymerases can displace RecA in this manner. Moreover, the initiation site for that synthetic round will now be 'blocked' instead. In such a situation, amplification is only linear with time, and will predominately generate single-stranded DNA amplification products. Thus, the described Zarling method, at best, is likely to generate little more than small quantities of ssDNA copies from each template. In addition, the linear amplification given by the Zarling method will only occur in the presence of SSB, since the displaced strand will continue to bind to the second interaction site on RecA, and single-stranded DNA will not be released (Mazin, A. V. and Kowalczykowski, S. C. (1998). Embo J 17, 1161-8). This probably explains why the Zarling method observed additional faster-migrating fragments when they included SSB. These additional fragments were most likely displaced single-stranded fragments. Hence, in the Zarling method only linear amplification of single-stranded DNA will occur. There is, therefore, a need in the art for an improved recombinase-dependent DNA amplification method.

This invention utilizes two new amplification strategies that avoid any requirement for thermal melting of DNA or thermostable components. These strategies also overcome the inefficiencies of the Zarling method. As with the Zarling strategy, these methods rely on the biological properties of the bacterial RecA protein, or its prokaryotic and eukaryotic relatives. However, in contrast to the Zarling method, these methods are devised to achieve exponential amplification of dsDNA. They achieve this by permitting rapid regeneration of targetable sequences in the target nucleic acid in the presence of dynamic RecA/DNA filaments. Furthermore one of the methods obviates any requirement for phased replication initiation from both ends of the target nucleic acid by coupling leading and lagging strand synthesis to simultaneously generate 2 double-stranded products.

BRIEF DESCRIPTION OF THE INVENTION

The invention provides a method of DNA amplification, termed RPA, which comprises the following steps. First, a recombinase agent is contacted with a first and a second nucleic acid primer to form a first and a second nucleoprotein primer. Second, the first and second nucleoprotein primers are contacted to a double stranded target sequence to form a first double stranded structure at a first portion of said first strand and form a double stranded structure at a second portion of said second strand so the 3' ends of said first nucleic acid primer and said second nucleic acid primer are oriented towards each other on a given template DNA molecule. Third, the 3' end of said first and second nucleoprotein primers are extended by DNA polymerases to generate first and second double stranded nucleic acids, and first and second displaced strands of nucleic acid. Finally, the second and third steps are repeated until a desired degree of amplification is reached.

The invention also provides for a method of nested RPAs. In a nested RPA, a first region of nucleic acid is amplified by RPA to form a first amplified region. Then a second region of nucleic acid that is completely within the first amplified region is amplified using RPA to form a second amplified region. This process may be repeated as often as necessary. For example, a third region of nucleic acid, which is completely within the second region, may be amplified from the second amplified region by RPA. In addition to the one, two and three rounds of RPA discussed above, the invention contemplates at least 4, and preferably at least 5 rounds of nested RPAs also.

The invention also provides for methods of detecting a genotype using RPA. This method is useful for genotyping, for detecting a normal or diseased condition, a predisposition or a lack of a disposition for a diseased condition. Further, RPA can be used for detecting the presence of a genome, such as for example, a genome of a pathogen. In this use, the method is useful for diagnosis and detection.

Prior to the addition of template DNA and/or Polymerase, RecA and SSB will compete for binding to single-stranded oligonucleotide primers. In the presence of a RecR and RecO, RecA is selectively stabilized onto the single-stranded primers forming RecA nucleoprotein filaments in a complex with RecO and RecR. This complex is competent to invade double-stranded DNA to form a D-loop at sites homologous to the oligonucleotide primers. Alternatively, RecA, RecO and RecR can be pre-loaded onto oligonucleotide primers prior to the introduction of SSB to the reaction mixture.

Figure 2B:
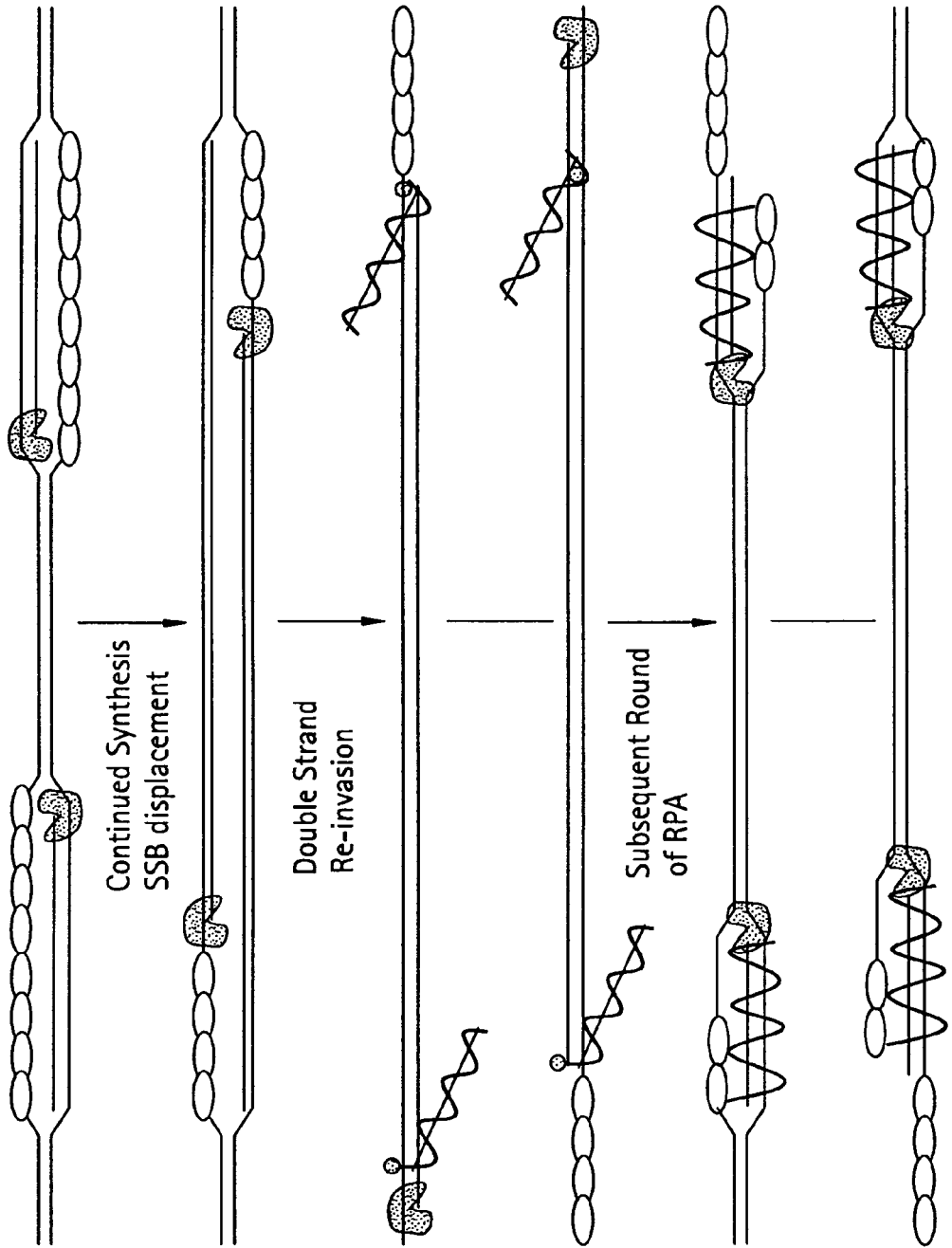

FIGS. 2A-2B depicts a schematic of succeeding steps, shown in panels (a) and (b) of Leading Strand Recombinase Polymerase Amplification (lsRPA).

RecA/primer nucleoprotein filaments invade double stranded template DNA preferentially associating with homologous target sites. As D-loops are formed and synthesis proceeds displaced single stranded DNA becomes coated with SSB. RecA release from double-stranded DNA can occur via ATP hydrolysis in a 5'-3' direction or as a result of helicase/resolvase or polymerase activity.

As synthesis continues, polymerases encounter SSB bound, displaced, single-stranded template. Double-stranded target site are re-invaded by RecA/primer nucleoprotein filaments. Subsequent rounds of lsRPA proceed from re-invaded sites.

FIGS. 3A-3D depicts a schematic of succeeding steps, shown in panels (a) (b) (c) and (d), of Leading and Lagging Strand Recombinase Polymerase Amplification.

Figure 3A:
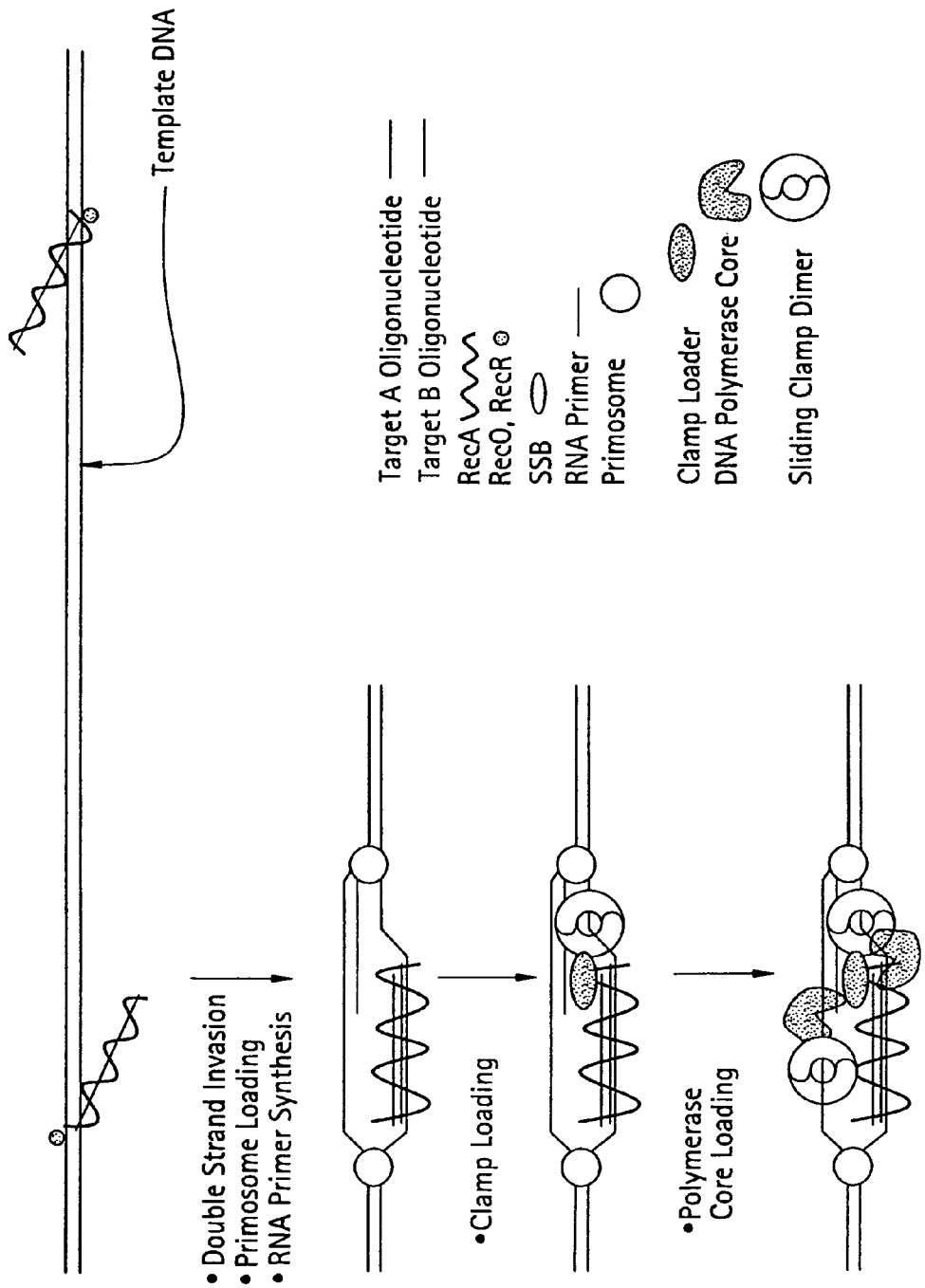

FIG. 3A. Leading/Lagging Strand Recombinase—Polymerase Amplification: Initiation. First, the primosome loads onto the D-loop formed by RecA nucleoprotein filament invasion. The primosome synthesizes a stretch of RNA primer. Finally, primosome recruits the clamp loader, which recruits both the sliding clamp dimer and the asymmetric DNA polymerase core.

Figure 3B:
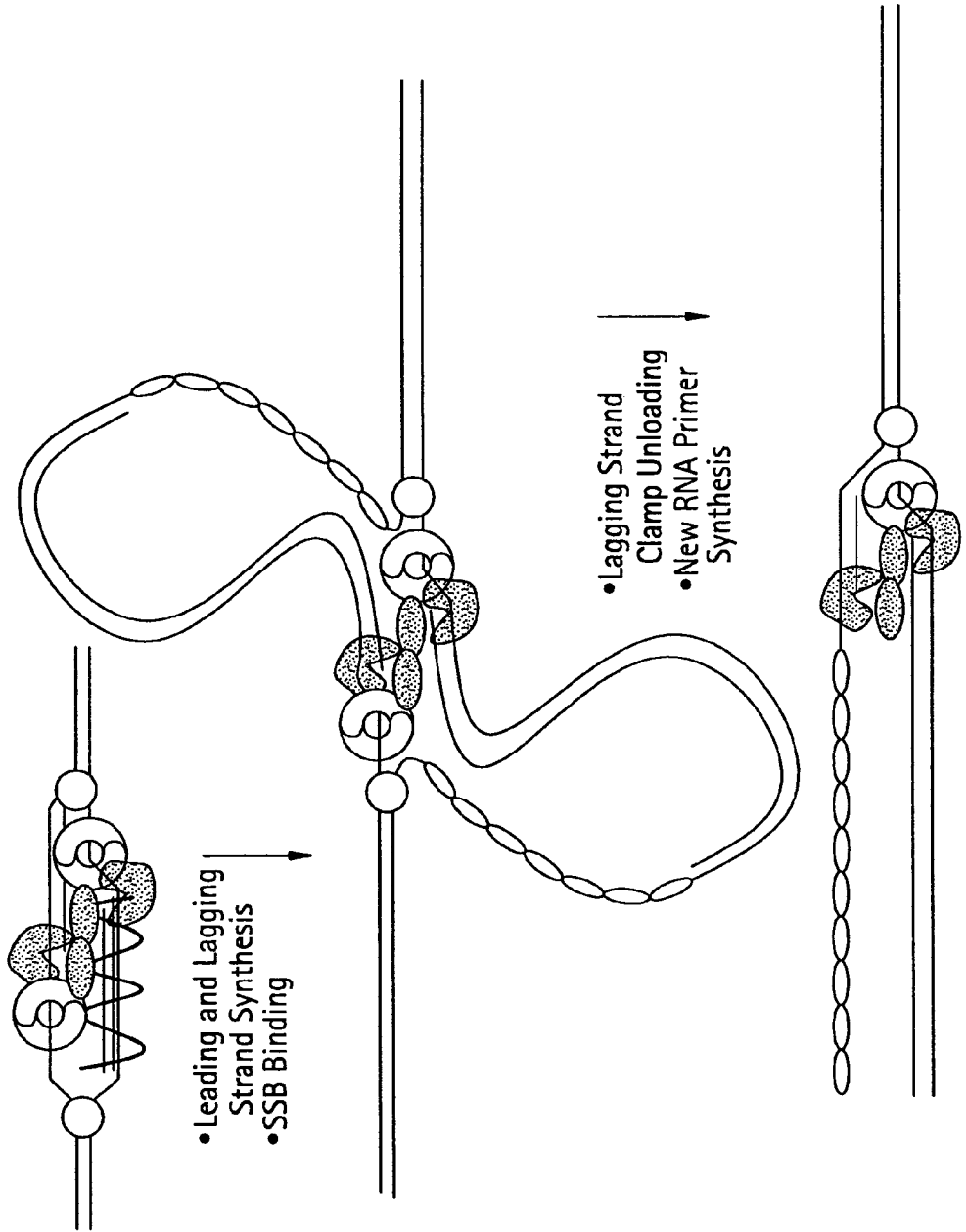

FIG. 3B. Leading/Lagging Strand Recombinase—Polymerase Amplification: Synthesis. Synthesis occurs simultaneously in both the leading and lagging directions. Eventually lagging strand synthesis stops and the lagging strand clamp is unloaded. Synthesis of the leading strand continues until a new site of lagging strand synthesis is formed.

FIG. 3C. Leading/Lagging Strand Recombinase—Polymerase Amplification. While leading strand synthesis continues, a new site of lagging strand synthesis is formed. Lagging strand synthesis continues back to the previous Okazaki fragment where the lagging strand claim is unloaded.

FIG. 3D. Leading/Lagging Strand Recombinase—Polymerase Amplification. Polymerase I removes the RNA primer and fills in the gap while DNA ligase connects the two Okazaki fragments forming a continuous lagging strand.

FIG. 4 depicts an example of nested primers chosen for nested RPA.

Figure 5:
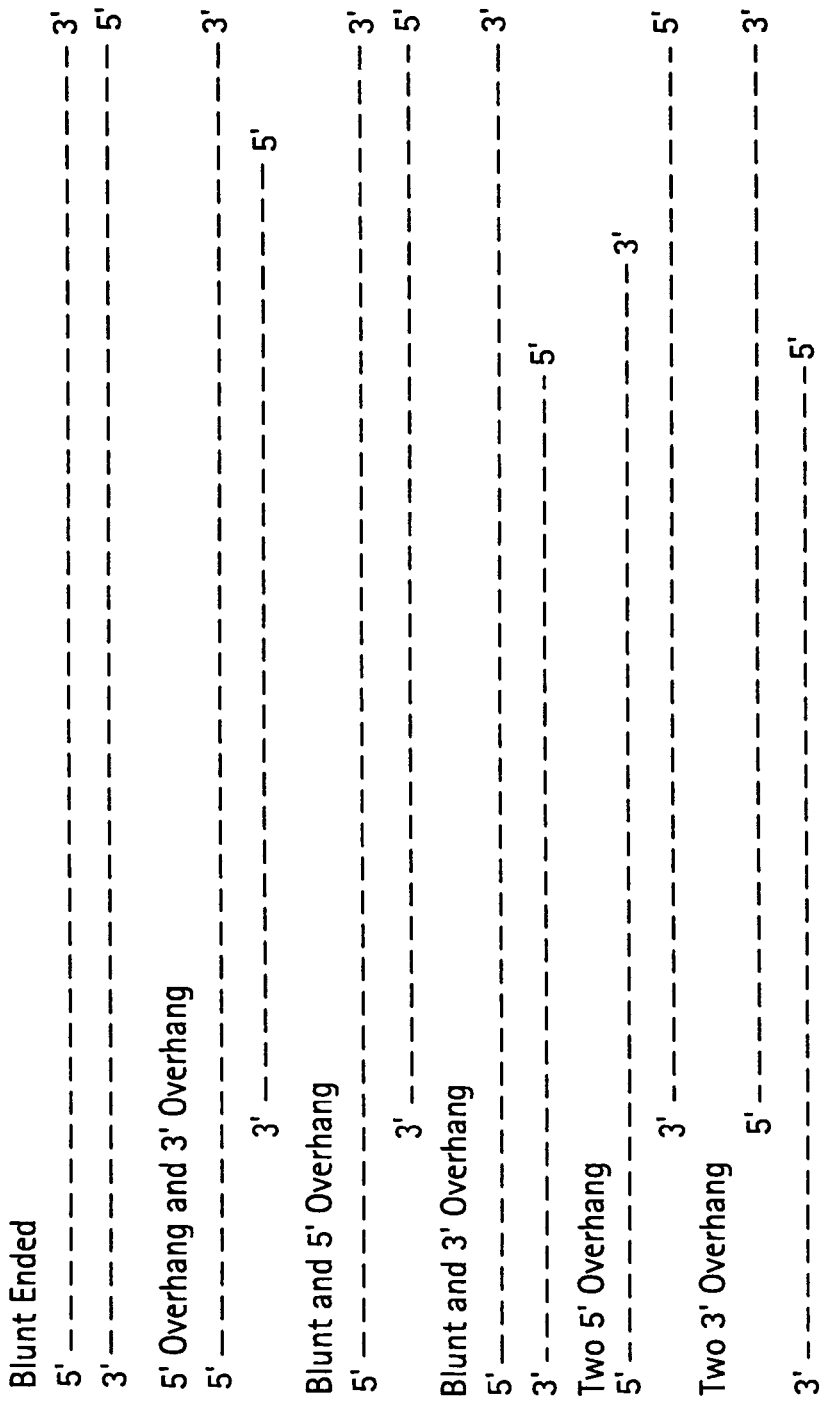

FIG. 5 depicts examples of suitable double stranded template nucleic acids.

Figure 6A:
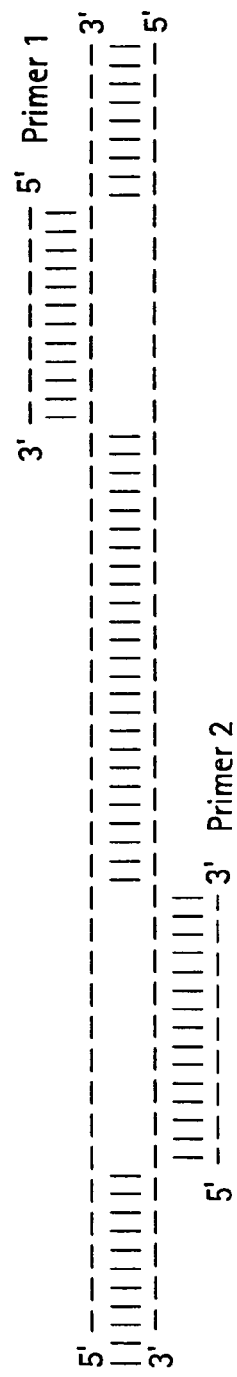
Figure 6B:
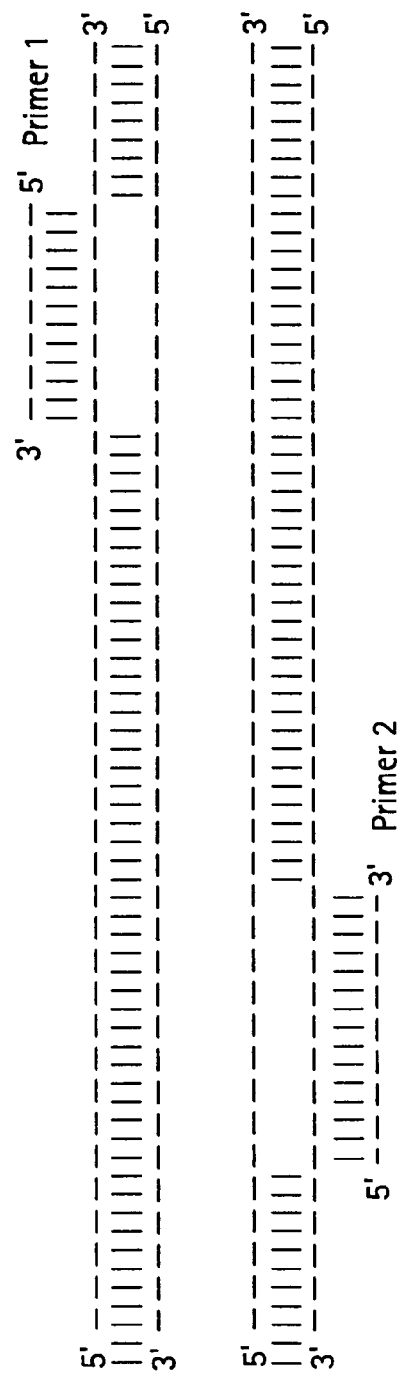

FIGS. 6A-6B depicts in panels (a) and (b) the various orientations of the RPA primer pairs in hybridization with the target nucleic acid.

Figure 7A:
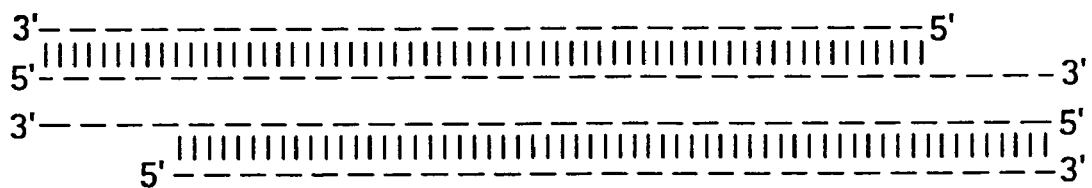
Figure 7B:
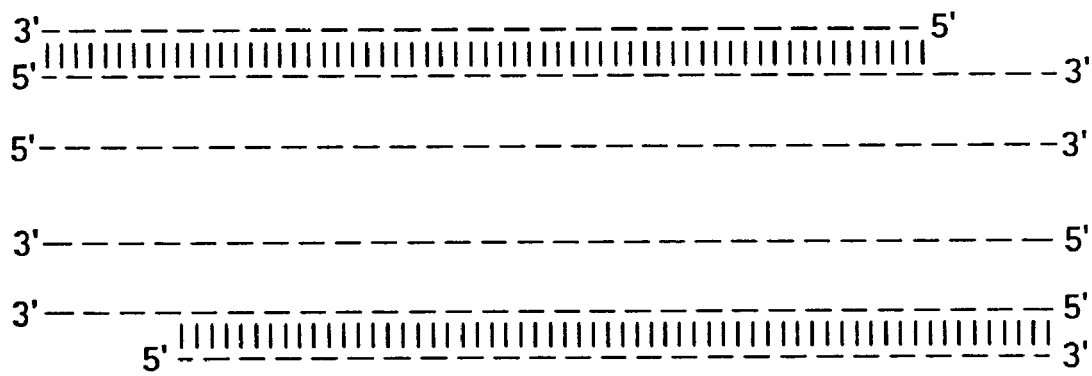
Figure 7C:
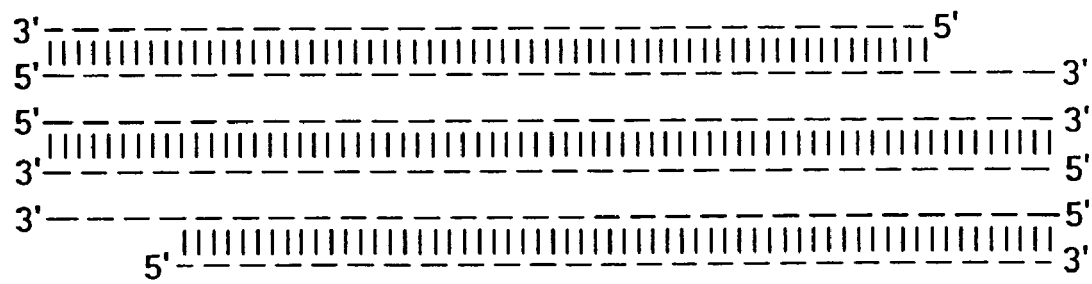

FIGS. 7A-7C panels (a), (b) and (c) depicts a schematic representation of an RPA reaction in progress.

Figures 8A, 8B, 8C:
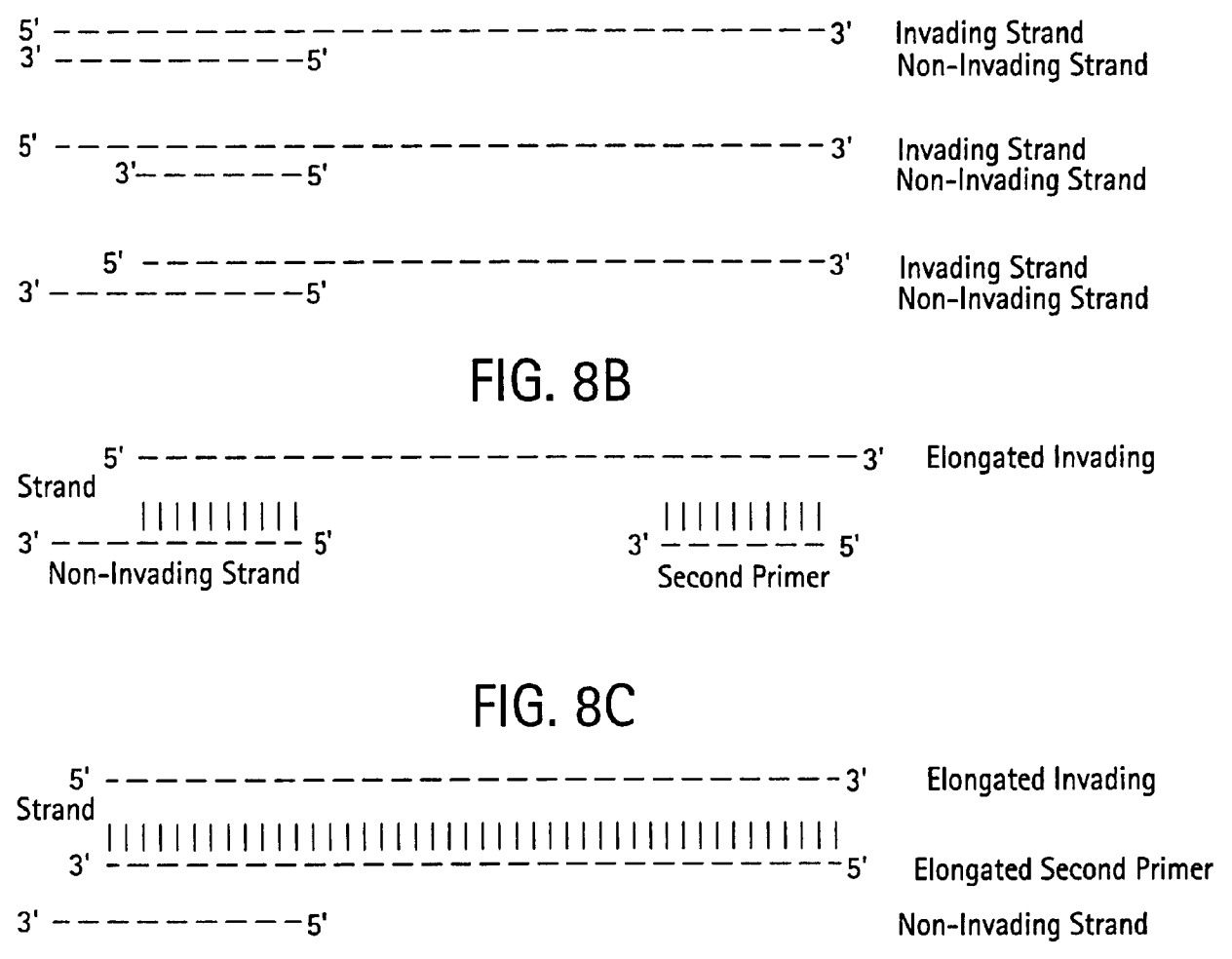

FIGS. 8A-8C depicts (a) examples of double stranded primers (b) double stranded primers after elongation and after annealing of the second member of a primer pair (c) after the elongation of the second member of a primer pair with the non-invading strand displaced.

DETAILED DESCRIPTION OF THE INVENTION

The present invention provides for Recombinase-Polymerase Amplification (RPA)—a method for the amplification of target nucleic acid polymers. One benefit of RPA is that it may be performed without the need for thermal melting of double-stranded templates therefore, the need for expensive thermocyclers is also eliminated. The present invention describes two related strategies by which RPA can be configured to permit exponential amplification of target nucleic acid polymers.

Leading Strand Recombinase-Polymerase Amplification (lsRPA)

In leading strand Recombinase-polymerase Amplification (lsRPA) single-stranded, or partially single-stranded, nucleic acid primers are targeted to homologous double-stranded, or partially double-stranded, sequences using recombinase agents, which would form D-loop structures. The invading single-stranded primers, which are part of the D-loops, are used to initiate polymerase synthesis reactions. A single primer species will amplify a target nucleic acid sequence through multiple rounds of double-stranded invasion followed by synthesis. If two opposing primers are used, amplification of a fragment—the target sequence—can be achieved. lsRPA is described briefly in FIGS. 1 and 2.

The target sequence to be amplified, in any of the methods of the invention, is preferably a double stranded DNA. However, the methods of the invention are not limited to double stranded DNA because other nucleic acid molecules, such as a single stranded DNA or RNA can be turned into double stranded DNA by one of skill in the arts using known methods. Suitable double stranded target DNA may be a genomic DNA or a cDNA. An RPA of the invention may amplify a target nucleic acid at least 10 fold, preferably at least 100 fold, more preferably at least 1,000 fold, even more preferably at least 10,000 fold, and most preferably at least 1,000,000 fold.

The target sequence is amplified with the help of recombinase agents. A recombinase agent is an enzyme that can coat single-stranded DNA (ssDNA) to form filaments, which can then scan double-stranded DNA (dsDNA) for regions of sequence homology. When homologous sequences are located, the nucleoprotein filament (comprising the recombinase agent) strand invades the dsDNA creating a short hybrid and a displaced strand bubble known as a D-loop. Suitable recombinase agents include the $E.$ $coli$ RecA protein or any homologous protein or protein complex from any phyla. These RecA homologues are generally named Rad51 after the first member of this group to be identified. Other recombinase agents may be utilized in place of RecA, for example as RecT or RecO. Recombinase agents generally require the presence of ATP, ATPγS, or other nucleoside triphosphates and their analogs. It is preferred that recombinase agents are used in a reaction environment in which regeneration of targeting sites can occur shortly following a round of D-loop stimulated synthesis. This will avoid a stalling of amplification or inefficient linear amplification of ssDNA caused by oscillating single-sided synthesis from one end to the other.

Naturally, any derivatives and functional analogs of the recombinase agent above may also function itself as a recombinase agent and these derivatives and analogs are also contemplated as embodiments of the invention. For example, a small peptide from recA which has been shown to retain some aspects of the recombination properties of recA may be used. This peptide comprise residues 193 to 212 of $E.$ $coli.$ recA and can mediate pairing of ssoligos (Oleg N. Voloshin, Lijang Wang, R. Daniel Camerini-Otero, Homologous DNA pairing Promoted by a 20-amino Acid Peptide Derived from RecA. Science Vol. 272 10 May 1996).

Since the use of ATPγS results in the formation of stable Recombinase-agent/dsDNA complexes that are likely incompatible with efficient amplification, it is preferable to use ATP and auxiliary enzymes to load and maintain the Recombinase-agent/ssDNA primer complexes. Alternatively, the limitations of the use of ATPγS may be overcome by the use of additional reaction components capable of stripping recA bound to ATPγS from exchange complexes. This role might be played by helicases such as the RuvA/RuvB complex.

The terms 'nucleic acid polymer' or 'nucleic acids' as used in this description can be interpreted broadly and include DNA and RNA as well as other hybridizing nucleic-acid-like molecules such as those with substituted backbones e.g. peptide nucleic acids (PNAs), morpholino backboned nucleic acids, or with modified bases and sugars.

In a preferred embodiment, RPA is performed with several auxiliary enzymes that can promote efficient disassembly of Recombinase-agent/dsDNA complexes after DNA synthesis initiation. These auxiliary enzymes include those that are capable of stimulating 3' to 5' disassembly and those capable of supporting 5' to 3' disassembly.

Auxiliary enzymes include several polymerases that can displace RecA in the 3' to 5' direction and can stimulate 3' to 5' disassembly of Recombinase-agent/dsDNA complexes (Pham et al., 2001). These DNA polymerase include *E. coli* PolV and homologous polymerase of other species. Normally in the life of *E. coli*, displacement of RecA in the 3' to 5' direction occurs as part of SOS-lesion-targeted synthesis in concert with SSB, sliding clamps and DNA polymerase. The polymerase essential for this activity in *E. coli* is PolV, a member of the recently discovered superfamily of polymerases including UmuC, DinB, Rad30 and Rev1, whose function in vivo is to copy DNA lesion templates. Critical to RPA, the in vitro 3' to 5' disassembly of RecA filaments cannot be catalyzed by PolI, PolIII or PolIV alone. Only PolV, in concert with SSB, has measurable ATP-independent 3' to 5' RecA/dsDNA disassembly activity. In effect, PolV pushes and removes RecA from DNA in a 3' to 5' direction ahead of the polymerase (Pham et al., 2001; Tang et al., 2000). Inclusion of PolV or a functional homologue may improve the amplification efficiency.

Other auxiliary enzymes include a class of enzymes called helicases which can be used to promote the disassembly of RecA from dsDNA. These promote disassembly in both the 5' to 3' and 3' to 5' directions. Helicases are essential components of the recombination process in vivo and function to move the branch points of recombination intermediates from one place to another, to separate strands, and to disassemble and recycle components bound to DNA. After the first round of invasion/synthesis has occurred in RPA, two new DNA duplexes are "marked" by the presence of RecA bound over the site to which primers must bind for additional rounds of synthesis. In such a situation dsDNA tends to occupy the high affinity site in RecA until it is actively displaced, either by ATP-dependent dissociation in the 5' to 3' direction, which may be limiting, or by 3' to 5' dissociation by some other active process. An ideal helicase complex for stimulating disassembly of RecA from intermediates consists of the *E. coli* proteins RuvA and RuvB. The RuvAB complex promotes branch migration, and dissociates the RecA protein, allowing RecA to be recycled (Adams et al., 1994). Normally, the RuvAB complex is targeted to recombination intermediates, particularly Holliday junction-like structures. As it works the RuvAB complex encircles DNA and forces RecA from the DNA in an ATP-driven translocation (Cromie and Leach, 2000; Eggleston and West, 2000). This RecA dissociation activity has been demonstrated using supercoiled dsDNA bound with RecA, which does not even possess Holliday junctions (Adams et al., PNAS 1994). The RuvAB complex can recognize branched structures within the RecA coated DNA. Incorporation of RuvAB into the RPA mixture will promote the dissociation of RecA from dsDNA following strand exchange and displacement, allowing renewed synthesis of the duplicated template from the same site. Additionally, the RuvAB complex can act in concert with RuvC, which finally cuts and resolves Holliday junctions. With RuvC added to the RPA reaction mixture, complicated structures such as Holliday junctions formed at invasion sites, can be resolved. Resolvase activity, such as that provided by RuvC, is particularly important when the targeting oligonucleotides are partially double-stranded. In such situations reverse branch migration can generate Holliday junctions, which can then be resolved by the RuvABC complex, to generate clean separated amplification products.

Still other auxiliary enzymes include the *E. coli* RecG protein. RecG can stimulate disassembly of branch structures. In vivo this protein functions to reverse replication forks at sites of DNA damage by unwinding both leading and lagging strands driving the replication fork back to generate a 4-way junction (Cox et al., 2000; Dillingham and Kowalczykowski, 2001; Singleton et al., 2001). In vivo such junctions function as substrates for strand switching to allow lesion bypass. In vitro RecG will bind to D-loops, and will lead to a decrease in D-loop structures by driving reverse branch migration. RecG prefers a junction with double-stranded elements on either side, hence partly double-stranded targeting oligonucleotides, homologous to the targeting site in both single-stranded and double-stranded regions, would be ideal. This would stimulate reverse branch migration and formation of a Holliday junction, which can be resolved by the RuvABC complex. In vivo RecG and RuvAB may compete to give different outcomes of recombination since branch migration will be driven in both directions (McGlynn and Lloyd, 1999; McGlynn et al., 2000). In both cases the proteins target junction DNA coated with RecA, and disassemble it in an active manner.

Other auxiliary enzymes useful in an RPA reaction mixture are those that allow continual generation of RecA nucleoprotein filaments in the presence of ATP and SSB. In order to allow removal of RecA at the appropriate moments, it is preferred to use ATP rather than ATPγS in an RPA reaction. Unfortunately RecA/ssDNA filaments formed with ATP spontaneously depolymerize in the 5' to 3' direction, and in the presence of SSB, as required here, repolymerization will not occur at significant rates. The solution to this problem is the use of the RecO, RecR and possibly RecF proteins. In the presence of SSB and ATP, RecA/ssDNA filaments dissociate (Bork et al., 2001; Webb et al., 1995; Webb et al., 1997; Webb et al., 1999). If RecA/ssDNA is incubated in the presence of RecO and RecR proteins this dissociation does not occur. Indeed the RecR protein remains associated with the filament and stabilizes the structure indefinitely. Even if ssDNA is bound by SSB, in the presence of RecR and RecO, filaments of RecA can reassemble displacing SSB. Thus it is possible to obviate the use of ATPγS, if necessary, by using ATP in the presence of RecO and RecR to maintain RecA/ssDNA filament integrity. The RecF protein interacts with the RecO and RecR system in a seemingly opposing manner. RecF competes with RecR tending to drive filament disassembly in vitro. It is likely that all three components in vivo function together to control the generation of invading structures, while limiting the extent of RecA coating of ssDNA. In another preferred embodiment, RecF is included in RPA reactions at an appropriate concentration to re-capitulate the dynamics of the in vivo processes. In addition, RecF may facilitate dissociation of RecA-coated intermediates after invasion has occurred.

As described, the use of ATP rather than ATPγS, and/or the use of displacing polymerases and helicases (e.g. the RuvA/RuvB complex), RecO, RecR and RecF should permit exponential amplification of double-stranded DNA by driving continual regeneration of targeting sites. This method, however, remains responsive to differences in initiation rate that might occur at the two opposing targeting sites. Such differences may lead to a decrease in amplification efficiency, and to the production of some single-stranded DNA. The PCR method largely avoids these complications because temperature cycling leads to coordinated synthesis from either side. In another embodiment, a situation analogous to the PCR condition just described may be induced by using temperature sensitive (ts) mutants of RecA that are non-functional at 42°

C., but function at lower temperatures in the range 25 to 37° C. (Alexseyev et al., 1996; Hickson et al., 1981). In this case, synthesis from either end can be synchronized by periodic lowering to the permissive temperature and then raising the reaction to a temperature non-permissive for the mutant RecA protein function, but permissive for the other components. By performing RPA with tsRecA mutants in combination with cycling of reaction temperatures, the number of molecules of DNA produced can be controlled. While this will require some mechanism to provide temperature cycling, the temperatures are well below those that would require the use of thermophile-derived proteins. Indeed, a simple chemical-based or portable low-power temperature-cycling device may be sufficient to control such reaction cycles.

RPA, as all other present-day nucleic acid amplification methods, employs polymerases to generate copies of template nucleic acid molecules. It is a necessity of most nucleic acid polymerases that incorporation requires a free 3'-hydroxyl moiety on the terminal sugar of a short stretch of double-stranded nucleic acid adjacent to the site of new synthesis. This stretch of double-stranded nucleic acid is typically formed on a template by a short complementary sequence, called a primer, which serves as an initiation site for the polymerase synthesis reaction. In some cases a 3' modification, such as a sulfydryl, may utilized to prime the synthesis reaction. The primer nucleic acid, which is base-paired with the template and extended by the polymerase, can be RNA or DNA. In vivo during genomic DNA replication, RNA primer sequences are synthesized de novo onto template DNA by primase enzymes. Typically, for in vitro reactions the primer is supplied as a short, often chemically synthesized, single-stranded DNA (or modified DNA or RNA), and is usually referred to as an oligonucleotide primer. The primer is often of a specific sequence, although random primers can also be used. The primer is targeted to complementary sequences by virtue of its specific base-pairing capacity. Formation of hybrids between the oligonucleotide primer and target nucleic acid are typically formed by incubation of the two in solution under conditions of salt, pH and temperature that allow spontaneous annealing.

In the case of the PCR the oligonucleotide primer is usually in vast excess for two main reasons. First, the high concentration will drive rapid annealing. Second, as the reaction proceeds through rounds of melting, annealing and extension the primer is consumed and becomes limiting. PCR targeted nucleic acids are often initially double-stranded in character, and if not, become double stranded following the first synthetic cycle. Such double-stranded molecules cannot anneal new oligonucleotides at temperature and solvent conditions appropriate for the catalytic activity and stability of most prokaryotic and eukaryotic proteins. Consequently, in order to allow cycles of amplification the original template and the newly synthesized strands must be first separated before annealing can occur once again. In practice this is achieved by thermal melting. For PCR, temperatures of at least 80° C. are required for thermal melting of most double-stranded nucleic acid molecules of lengths greater than 100 base pairs. In most PCR protocols a temperature of 90 to 100° C. is applied to melt the DNA. Such temperatures allow only rare thermostable enzymes to be used. These polymerases are typically derived from thermophilic prokaryotes.

The advantage of RPA is that it allows the formation of short stretches of double-stranded nucleic acids bearing a free 3'—OH for extension from double-stranded templates without thermal melting. This is achieved by using the RecA protein from E. coli (or a RecA relative from other phyla). In the presence of ATP, dATP, ddATP, UTP, ATPγS, and possibly other types of nucleoside triphosphates and their analogs, RecA will form a nucleoprotein filament around single-stranded DNA. This filament will then scan double-stranded DNA. When homologous sequences are located RecA will catalyze a strand invasion reaction and pairing of the oligonucleotide with the homologous strand of the target DNA. The original pairing strand is displaced by strand invasion leaving a bubble of single stranded DNA in the region.

RecA protein can be obtained from commercial sources. Alternatively it can be purified according to standard protocols e.g. (Cox et al., 1981; Kuramitsu et al., 1981). RecA homologues have been purified from thermophilic organisms including *Thermococcus kodakaraensis* (Rashid et al., 2001), *Thermotoga maritima* (Wetmur et al., 1994), *Aquifex pyrophilus* (Wetmur et al., 1994), *Pyrococcus furiosus* (Komori et al., 2000), *Thermus aquaticus* (Wetmur et al., 1994), *Pyrobaculum islandicum* (Spies et al., 2000), and *Thermus thernophilus* (Kato and Kuramitsu, 1993). RecA has also been purified from other prokaryotes e.g. *Salmonella typhimurium* (Pierre and Paoletti, 1983), *Bacillus subtilis* (Lovett and Roberts, 1985), *Streptococcus pneumoniae* (Steffen and Bryant, 2000), *Bacteroides fragilis* (Goodman et al., 1987), *Proteus mirabilis* (West et al., 1983), *Rhizobium meliloti* (Better and Helinski, 1983), *Pseudomonas aeruginosa* (Kurumizaka et al., 1994), from eukaryotes e.g. *Saccharomyces cerevisiae* (Heyer and Kolodner, 1989), *Ustilago maydis* (Bennett and Holloman, 2001), including vertebrates e.g. Human Rad51 (Baumann et al., 1997) and *Xenopus laevis* (Maeshima et al., 1996), as well as plants including broccoli (Tissier et al., 1995).

For clarity of description, leading strand Recombinase-Polymerase Amplification method (lsRPA) can be divided into four phases.

1) Sequence Targeting

RPA is initiated by targeting sequences using synthetic oligonucleotides coated with RecA, or a functional homologue. In order to permit exponential amplification two such synthetic oligonucleotides would be employed in a manner such that their free 3'-ends are orientated toward one another. Nucleoprotein filaments comprising these oligonucleotides and RecA protein will identify targets in complex DNA rapidly and specifically. Once targeted the RecA protein catalyses strand exchange such that D-loop structures are formed. It may be necessary to use ATP rather than ATPγS in the procedure for efficient amplification. If ATP is used, RecO, RecR, and/or RecF, molecules may prove essential for efficient amplification.

2) Initiation of DNA Synthesis

DNA polymerases will detect and bind to the hybrid between the invading oligonucleotides and the template DNA and initiate DNA synthesis from the free 3'-hydroxyl exposed in the hybrid. Exposure of this 3'-hydroxyl, and subsequent DNA synthesis, will likely require disassembly of RecA protein from the double-stranded hybrid formed by strand exchange. To attain this disassembly it will probably be necessary to employ ATP, which can support spontaneous disassembly of RecA from invasion complexes. Additionally disassembly can be stimulated/enhanced by the use of other proteins contained within the reaction mixture such as RuvA, RuvB, RuvC, recG, other helicases, or other stimulatory components, which can act to strip RecA from the strand exchange product.

3) Strand Displacement DNA Synthesis and Replicon Separation.

As the DNA polymerases synthesize complementary copies of template DNAs using the free 3'-hydroxyls of invading oligonucleotides, or their partly extended products, the polymerases displace single-stranded DNAs, which may be coated with single strand binding proteins (SSB) included in the reaction. In an ideal configuration, invasion of oligonucleotides at both ends of the target nucleic acid sequence will occur in similar timeframes, such that two polymerases on the same template nucleic acid will initially progress toward one another. When these extending complexes meet one another, the original template should simply fall apart, and the polymerases will continue to synthesize without a need for strand displacement, now copying SSB-bound ssDNA template. Because of steric hinderance, polymerases may become dissociated from the template temporarily when the polymerases meet to permit the separation of the two template strands 4) Completion of Synthesis and Re-Invasion.

Once the template strands have separated, polymerases can complete the extension to the end of the template (or past the sequence acting as the second, facing, targeting site if the initial template is longer than the desired product). To permit exponential amplification it is necessary for new products to be targeted and replicated in a manner similar to the original templates, that is from both targeted ends. The newly synthesized targeted site will be freely available to targeting RecA/oligonucleotide filaments. The site initially used to prime synthesis should also have been freed as a consequence of the use of conditions in the reaction that favor disassembly of RecA from strand exchange products. Providing the re-invasion at this latter site occurs in less time than it takes the polymerase to synthesize past the second targeting site, be primed at that second site, and return to the first site, then single-stranded DNA will not be the primary product and exponential amplification will occur. Having multiple synthetic complexes operating on the same template raises the possibility that very short amplification times can be achieved.

Recombinase-Polymerase Amplification (RPA) Using Simultaneous Leading and Lagging Strand Synthesis In our description of (leading strand RPA) lsRPA we detail a multi-component system with the capacity to regenerate targeting sequences thus permitting exponential amplification of double-stranded DNA. Unlike the Zarling method, lsRPA avoids the linear production of single-stranded DNA. There is another approach to solving this problem that completely avoids the possibility of single-stranded products and a requirement for simultaneous end initiation. This method necessarily involves a more complex reaction mixture. Nevertheless all of the required components are now well understood and should be amenable to assembly into a single system. This system will recapitulate events occurring during the normal replication cycle of cells to permit coupled leading and lagging strand synthesis. This method, leading/lagging strand RPA is described briefly in FIGS. 1 and 3.

During normal replication in vivo, double-stranded DNA is simultaneously separated into 2 strands and both are copied to give 2 new molecules of double-stranded DNA by a replication machine. This 'machine' couples conventional 5' to 3' leading strand synthesis with lagging strand synthesis, in which short RNA primers are synthesized onto template nucleic acids by primase enzymes. During lagging strand synthesis, short fragments of DNA are produced, called Okazaki fragments, which are ligated together to form contiguous lagging strands. This simultaneous leading-strand/lagging-strand synthesis is responsible for duplication of the entire genome of prokaryotic and eukaryotic organisms alike. The essential components of this system have been identified and characterized biochemically. The components can be assembled in vitro to achieve a more efficient amplification than possible using only leading-strand synthesis.

The essential components of the replication 'machine' are now well characterized for $E.\ coli$. This machine comprises the PolIII holoenzyme (Glover and McHenry, 2001; Kelman and O'Donnell, 1995) and the primosome (Benkovic et al., 2001; Marians, 1999). The PolIII holoenzyme is made up of ten polypeptide components. Each holoenzyme contains two, asymmetrically oriented, core structures, each consisting of a polymerase ($\alpha$ subunit) and two additional core components the $\epsilon$ subunit, which possesses 3' to 5' exonuclease activity, and the $\theta$ subunit. In addition to the core complex another set of polypeptides provide the holoenzyme with processivity and couple leading and lagging strand synthesis. The $\beta$-dimer sliding clamp encircles the template DNA affixing the complex to the template with extremely high affinity. The sliding clamp loaded onto DNA by the DnaX clamp loader comprising the $\tau_2\gamma\delta\delta'\chi\psi$ polypeptide subunits.

For clarity of description, the RPA method can be divided into four phases. In reality all phases will occur simultaneously in a single reaction.

1) Sequence Targeting

RPA is initiated by targeting sequences using synthetic oligonucleotides coated with RecA, or a functional homologue. Such nucleoprotein filaments will identify targets in complex DNA rapidly and specifically. Once targeted, the RecA protein catalyses strand exchange such that a D-loop structure is formed. It may be necessary to use ATP rather than ATPγS in the procedure for efficient amplification. The linkage of leading and lagging strand syntheses however may obviate the requirement for very rapid RecA stripping after initiation of synthesis. If ATP is used, RecO, RecR, and RecF molecules may prove essential for efficient amplification.

2) Primosome Assembly

Primosomes can be assembled at D-loops. Normally, D-loop structures are formed by RecA as part of the mechanism to rescue damaged DNA in vivo, or during other forms of recombination. The purpose of the combined action of RecA-mediated strand exchange and primosome assembly is to generate a replication fork. A replication fork is the nucleoprotein structure comprising the separated template DNA strands and the replisome. The replisome consists of the polymerase holoenzyme complex, the primosome, and other components needed to simultaneously replicate both strands of template DNA. Primosomes provide both the DNA unwinding and the Okazaki fragment priming functions required for replication fork progression.

Primosome assembly has been studied intensively through genetic and biochemical analysis in $E.\ coli$. The minimal set of polypeptides required for this process is well known and exist as purified components. The primosome assembly proteins are PriA, PriB, PriC, DnaT, DnaC, DnaB and DnaG. These proteins have been shown sufficient to assemble a primosome complex on bacteriophage ΦX174 DNA in vitro (Kornberg and Baker, 1992; Marians, 1992). PriA binds to the primosome assembly site (PAS) on the ΦX174 chromosome. Then PriB, DnaT, and PriC bind sequentially to the PriA-DNA complex. PriB appears to stabilize PriA at the PAS and facilitate the binding of DnaT (Liu et al., 1996). PriC is only partially required for the full assembly reaction. Omission of PriC from the reaction will lower priming 3 to 4 fold (Ng and Marians, 1996a; Ng and Marians, 1996b). The function of PriC in the bacterium is genetically redundant to PriB. DnaC then loads DnaB into the complex in an ATP-dependent fashion. This PriABC-DnaBT complex is competent to translocate along the chromosome. The DnaG primase can interact transiently with the complex to synthesize RNA primers.

During replication in *E. coli*, DnaB and DnaG function as a helicase and primase respectively. These two components are continually required in association with the PolIII holoenzyme to synthesize primers for the Okazaki fragments. Hence, DnaB and DnaG are the core components of the mobile primosome associated with the replication fork. The other primosome components described are essential for assembly of the primosome onto DNA, and for associating a dimeric polymerase. The primosome assembly proteins are required for the re-establishment of replication forks at recombination intermediates formed by RecA and strand exchange. PriA can initiate assembly of a replisome, competent for DNA synthesis, on recombination intermediates. It is possible to target D-loops in vitro with a mixture of PriA, PriB and DnaT, which are then competent to incorporate DnaB and DnaC. Once a primosome has been formed at the D-loop, all that remains to initiate replication is to load a holoenzyme complex to the site.

3) Fork Assembly and Initiation of DNA Synthesis

Replication forks will assemble at the site of primosome assembly. The presence of a free 3'-end on the invading strand of the D-loop stimulates the DnaX clamp loader complex detailed earlier to assemble a β-dimer at this site to act as a sliding clamp. The holoenzyme and 2 core units are joined together by the scaffold τ subunit. The τ subunit also has interaction surfaces for the β-dimer, for the clamp loader, and for the DnaB helicase component of the primosome. These multiple interactions are necessary to coordinate synthesis of both leading and lagging strands using the 2 asymmetrically joined core polymerase complexes.

The primosomal primase, DnaG, synthesizes a short RNA primer onto the unwound lagging strand DNA template. In the presence of the holoenzyme, the clamp loader recognizes the RNA/DNA duplex and loads a second β-dimer clamp onto this site. The presence of an active primosome and the interaction of the τ subunit with DnaB are critical to ensure simultaneous leading/lagging strand synthesis. Without this interaction the polymerase will move away from the primosome site without coupling.

A replication fork is now assembled. Synthesis of both leading and lagging strand will now occur simultaneously, and the DnaB helicase will separate template strands ahead of the oncoming holoenzyme. The lagging strand holoenzyme core will generate Okazaki fragments of 1 to 2 kilobases in length. Once the lagging strand polymerase encounters the previous RNA primer, it dissociates from the β-clamp and synthesis is initiated from a newly assembled clamp loaded in the vicinity of the front of the leading strand. The same lagging strand holoenzyme core will be re-used since it is physically tethered to leading strand core.

There is a dynamic interaction between β-dimer clamps, core subunits and clamp loaders. Their affinities can switch depending upon the physical circumstances. The β-dimer that has been 'abandoned' at the end of the Okazaki fragments may be recycled via active removal by clamp loaders, or excess δ subunit that may be present.

The RNA primers at the ends of Okazaki fragments are removed by the 5' to 3' exonuclease activity of DNA polymerase I. DNA ligase then joins the Okazaki fragments together forming a continuous lagging strand.

4) Fork Meeting and Termination

In RPA, replication is initiated at two distant sites and the replication forks are oriented toward each other. As replication forks converge the two original template strands will dissociate from one another as they become separated entirely both behind, and in front, of each fork. The leading strand core of each fork will then complete synthesis, the remaining RNA primers will be processed, and the final products will be two double-stranded molecules. We can reasonably expect to amplify DNA's on the order of several Megabases (Mb) by such an approach. In this disclosure, megabase also encompasses megabasepairs. Based on the known synthetic rate of the PolIII holoenzyme we can expect the replication forks to proceed at a rate of approximately 1 Mb/1000 seconds, i.e., approximately 15 to 20 minutes per cycle for a 1 Mb fragment.

The final consideration is the mechanism by which rapid exponential amplification of DNA will be achieved. The key to this process will be to allow efficient reinvasion of the targeting sites by the use of mixtures of helicases, resolvases and the RecO, RecR, and RecF proteins. Under appropriate conditions reinvasion and primosome assembly should be possible shortly after a holoenzyme has moved away from the fork-assembly site. Continual invasions should present no problems since the DNA will simply become branched at many points. Each branch will naturally resolve as it encounters the oncoming fork. Under these conditions it may be possible to achieve enormous amplification in times similar to the time taken to replicate the DNA only once. It may be critical however to limit the concentrations of targeting oligonucleotides to avoid nucleotide depletion prior to the completion of synthesis.

In addition to the holoenzyme complex, the replication machine employs another complex known as the primosome, which synthesizes the lagging strand and moves the replication fork forwards. The primosome complex comprises a helicase encoded by DnaB and a primase encoded by DnaG. Finally, in addition to the proteins of the holoenzyme and primosome, replication requires the activity of single-stranded DNA binding protein (SSB), *E. coli* DNA polymerase I and DNA ligase. These latter two components are required to process Okazaki fragments.

Nested RPA:

In another embodiment, RPA amplification may be performed in a process referred to herein as "nested RPA."

A difficulty in detecting a rare sequence is that there can be a high ratio of non-target to target sequence. The ability of a RPA to discriminate between target and non-target DNA and amplify only target sequences is a key aspect of improved sensitivity. Discrimination between non-target and target is a reflection of the specificity of the primers and reaction conditions. The more specific a reaction is the greater the relative amount of the specific target sequence that is produced and the easier that product is to detect. An increase in specificity can, therefore, increase sensitivity as well.

The need for improved sensitivity and specificity can be addressed by using nested RPA. The nested RPA involves a first RPA of a first region of DNA. Then the reaction mixture is diluted, for example, by 10, 20, 30, 40, 50, 75, or 100 fold or more to reduce the concentration of the first primer pair, and a second primer pair is introduced into the reaction mixture and RPA repeated. According to one embodiment of the invention, the second primer pair is designed to be internal to the first primer pair to amplify a subsequence of the first RPA product. The method increases specific amplification, i.e., reduces non-specific background amplification products and therefore increases sensitivity. Such non-specific amplification products, although they arise by virtue of fortuitous partial homology to the flanking primers, are unlikely to also have sufficient homology to the nested primers to continue to amplify. Detection and specificity of RPA may be further improved by labeling one or both of the second primer pair such that only primers amplified with one or both of the second primer pair is detected.

Nested RPA is not limited to the use of two sets of primer. Naturally, more sets of primers may be used to increase specificity or sensitivity. Thus, three, four or five pairs of primers may be used. Furthermore, the different sets of primers, as another embodiment of the invention, may share common primers as illustrated in FIG. 4.

In FIG. 4, the primer sets are designed to be used sequentially. For example, a first RPA is performed with primer set 1, a second RPA using the amplified product of the first RPA is performed with a primer set 2, a third RPA using the amplified product of the second RPA is performed with a primer set 3, a fourth RPA using the amplified sequence of the third RPA is performed with a primer set 4, and finally, a fifth RPA is performed using the amplified product of the fourth RPA is performed with a primer set 5. In this case, primer set 1, 2, and 3, share a common primer—primer (a). Primer 3, 4, and 5 share a common primer—primer (b).

Nested RPA may be performed using any of the two RPA methods described as well as a combination of the two methods in any particular order. That is, RPA may be performed solely by leading strand RPA, solely by leading and lagging strand RPA, or a combination of leading strand RPA and leading and lagging strand RPA in any particular order.

One benefit of any of the RPA methods of the invention is the size of the amplified product. While current methods of amplification such as PCR are limited to an upper limit of about 10 Kb, RPA methods are capable of amplifying regions of nucleic acids of up to hundreds of megabases. For leading/lagging strand RPA, the sizes of a target sequence to be amplified can be hundreds of megabases, such as, for example, less than 500 megabases, less than 300 megabase, less than 100 megabase, less than 70 megabase, less than 50 megabase, less than 25 megabase, less than 10 megabase, less than 5 megabase, less than 2 megabass, less than one megabase, less than 500 kb, less than 200 kb, less than 100 kb, less than 50 kb, less than 25 kb, or less than 10 kb, less than 5 kb, less than 2 kb, less than 1 kb. For lsRPA, the sizes of a target sequence can be in the megabase range such as, less than 5 megabase, less than 2 megabass, less than one megabase, less than 500 kb, less than 200 kb, less than 100 kb, less than 50 kb, less than 25 kb, or less than 10 kb, less than 5 kb, less than 2 kb, less than 1 kb.

Selection of RPA Reagents and Reaction Parameters

The details of leading strand RPA, leading and lagging strand RPA, and nested RPA were listed above. This section will describe the selection of reagents and parameter for any of the three methods discussed above.

One benefit of RPA is that the amplified product of RPA is double stranded DNA which could be used for other molecular biology procedures. Thus, RPA may be combined with other methods in molecular biology. For example, the starting material for RPA may be a PCR amplified fragment. Alternatively, the product of an RPA may be used for PCR.

If necessary, the RPA products in any of the methods of the invention may be purified. For example, in the nested RPA method, the amplified product may be purified after each RPA step before a subsequent RPA step. Methods of purification of nucleic acids are known in the art and would include, at least, phenol extraction, nucleic acid precipitation (e.g., with salt and ethanol), column chromatography (e.g., size exclusion, ionic column, affinity column and the like) or any combination of these techniques.

As discussed, the primers used in RPA may be "double stranded" or "capable of forming double stranded structures."

These terms refer to DNA molecules that exist in a double stranded condition in a reaction solution such as a RPA reaction solution or a PCR reaction solution. The composition of a PCR solution is known. The composition of a RPA reaction is listed in this detailed description section and in the Examples.

The primers may have a single stranded region for hybridization to the target DNA in the presence of a recombinase agent. The single stranded region may be, for example, about 10 bases about 15 bases, about 20 bases, about 25 bases, about 30 bases, about 40 bases, and about 50 bases. Even longer regions such as about 75 bases, about 100 bases, about 150 base or more may be used but it is not necessary. The choice of single stranded regions will depend on the complexity of the starting nucleic acid so that for example, a human genome may require a longer primer while a plasmid may require a much shorter primer.

The two strands of nucleic acid in a double stranded DNA need not be completely complementary. For example, the double-stranded region of a double-stranded DNA may differ by up to 1% in sequence. That is, the sequence of two strands of nucleic acid may differ by one base in one hundred bases and would still exist in a double stranded condition in solution. Nucleic acids with 1% difference in their complementary sequence are contemplated as double stranded DNA for the purposes of this disclosure.

In addition, the target nucleic acid (i.e., the nucleic acid to be amplified by the RPA methods of the invention) may be partially double stranded and partially single stranded. For example, nucleic acid in any of the configuration of FIG. 5 would be suitable as a target nucleic acid of the invention. As discussed, the target nucleic acid may be RNA. RNA can be converted to double-stranded cDNA using known methods and the double-stranded cDNA may be used as the target nucleic acid. As shown if FIG. 5, the template nucleic acid may have any combination of ends selected from 3' overhang, 5' overhang, or blunt ends.

The lsRPA method of the invention comprises at least the following steps. First, a recombinase agent is contacted to two nucleic acid primers (referred to herein as a first and a second primer) to form two nucleoprotein primers (referred to herein as a first nucleoprotein primer and a second nucleoprotein primer).

Second, the first and second nucleoprotein primers are contacted to the template nucleic acid to form a double stranded structure at a first portion of the first strand and a second double stranded structure at a second portion of the second strand. The two primers are designed so that when hybridized, they are pointed at each other as illustrated in FIG. 6A. Alternatively, primer 1 and primer 2 may hybridize different target nucleic acids as illustrated in FIG. 6B.

Third, the nucleoprotein primers are extended at their 3' ends to generate a first and a second double stranded nucleic acid (FIG. 7A). Where the primers are hybridized to different target nucleic acids, the elongation of the primers will generate displaced strands (FIG. 7B). In this case, the two displaced strands that result from primer elongation may hybridize and form a new double stranded template nucleic acid (FIG. 7C).

Step two and three are repeated until the desired degree of amplification is reached. The process is a dynamic process in that primer hybridization to the target nucleic acid and elongation are allowed to proceed continuously. One advantage of this invention is that the amplification is performed continuously without the need for temperature cycling or enzyme addition after initiation of the reaction.

In an embodiment, steps two and three are repeated at least 5 times. Preferably, it is repeated at least 10 times. More preferably, it is repeated at least 20 times, such as at least 30 times. Most preferably, the two steps are repeated at least 50 times. For multiple repetitions of the amplification step (e.g., step 2 and 3) a RPA of the invention is preferably started with a primer to target nucleic acid ration of at least 100 to 1, preferably at least 300 to 1, and most preferably at least 1000 to 1. That is, there are at least 100, 300 or 1000 copies of the primer per copy of a target nucleic acid.

In an optional step, after a sufficient round of amplification, additional components may be added to the reaction after a period of time to enhance the overall amplification efficiency. In one embodiment, the additional components may be one or more of the following: recombinase agents, one or more primers, polymerase, and one or more of the additional agents (discussed in a separate section below).

In a preferred embodiment, a small fraction of a first RPA reaction is used as a supply of template DNA for subsequent rounds or RPA amplification. In this method, a first RPA amplification reaction is performed on a target nucleic acid. After the first RPA reaction, a small fraction of the total reaction is used as a substitute of the target nucleic acid for a subsequent round of RPA reaction. The fraction may be, for example, less than about 10% of the first reaction. Preferably, the fraction may be less than about 5% of the first reaction. More preferably, the fraction may be less than 2% of the first reaction. Most preferably, the fraction may be less than 1% of the initial reaction.

The primer used in RPA is preferably DNA although PNA, and RNA are also suitable for use as primers. It is noted that in fact, in DNA replication, DNA polymerases elongate genomic DNA from RNA primers.

Synthetic oligonucleotides may serve as DNA primer and can be used as substrates for formation of nucleoprotein filaments with RecA or its homologues. Sequences as short as 15 nucleotides are capable of targeting double-stranded DNA (Hsieh et al., 1992). Such oligonucleotides can be synthesized according to standard phosphoroamidate chemistry, or otherwise. Modified bases and/or linker backbone chemistries may be desirable and functional in some cases. Additionally oligonucleotides may be modified at their ends, either 5' or 3', with groups that serve various purposes e.g. fluorescent groups, quenchers, protecting (blocking) groups (reversible or not), magnetic tags, proteins etc. In some cases single-stranded oligonucleotides may be used for strand invasion, in others only partly single stranded nucleic acids may be used, the 5' stretch of sequence of an invading nucleic acid being already hybridized to an oligonucleotide.

In another embodiment of the invention, the primers may comprise a 5' region that is not homologous to the target nucleic acid. It should be noted that the processes of the invention should be functional even if the primers are not completely complementary to the target nucleic acid. The primers may be noncomplementary by having additional sequences at their 5' end. These additional sequences may be, for example, the sequence for a restriction endonuclease recognition site or the sequence that is complementary to a sequencing primer. The restriction endonuclease recognition site may be useful for subsequent cleavage of the amplified sequence. The use of restriction endonuclease that cleaves nucleic acid outside the restriction endonuclease recognition site is also contemplated. The sequence that is complementary for a sequencing primer may allow rapid DNA sequencing of the amplified product using commercially available primers or commercially available sequencing apparatus.

Formation of nucleoprotein filaments can be performed by incubation of the primer (oligonucleotides) with RecA protein or its homologues in the presence of ATP, and auxiliary proteins such as RecO, RecR and RecF. When incubated at 37° C. in RecA buffer (20 mM Tris-HCl pH 7.5, 10 mM $MgCl_2$, 2 mM ATP, 2 mM DTT and 100 ug/ml Bovine Serum Albumin), RecA will form helical filaments on ssDNA with 6 protomers per turn. The DNA is located within the interior of the protein helix. In the presence of dsDNA, the RecA/ssDNA nucleoprotein filament can scan DNA at rates of at least $10^7$ bp per hour. The mode of scanning is unclear but it is at a speed ($>10^3$ bp per second) that it may involve only the initial few base pairs that can be easily accessed along one face of the major groove. Successful binding may result in a transition to a triple-helical intermediate, which is then followed by strand invasion and displacement to form a D-loop. Such joint molecules can be formed under similar condition to those described above for formation of helical filaments, and hence in the presence of ssDNA, the homologous dsDNA, RecA, ATP, auxiliary proteins and suitable buffer and temperature conditions, joint molecules will form spontaneously. If ATP is used the assembly is reversible and will reach equilibrium, but RecA/ssDNA filaments can be stabilized, even in the presence of SSB, by the auxiliary proteins RecO and RecR. In the case of thermostable proteins the temperature of incubation can be higher. If a renewable supply of ATP is required a standard ATP regeneration system can be included in the reaction.

DNA polymerases can use the free 3'-hydroxyl of the invading strand to catalyze DNA synthesis by incorporation of new nucleotides. A number of polymerases can use the 3'-hydroxyl of the invading strand to catalyze synthesis and simultaneously displace the other strand as synthesis occurs. For example *E. coli* polymerase II or III can be used to extend invaded D-loops (Morel et al., 1997). In addition, *E. coli* polymerase V normally used in SOS-lesion-targeted mutations in *E. coli* can be used (Pham et al., 2001). All of these polymerases can be rendered highly processive through their interactions and co-operation with the β-dimer clamp, as well as single stranded DNA binding protein (SSB) and other components. Other polymerases from prokaryotes, viruses, and eukaryotes can also be used to extend the invading strand.

In another embodiment of the invention, the primer may be partially double stranded, partially single stranded and with at least one single stranded 3' overhang. In this embodiment, the primer may comprise a invading strand and a non-invading strand as shown in FIG. 8A. In this case, after the invading strand is hybridized to the target DNA and elongated, it serves as a target nucleic acid for a second primer as shown in FIG. 8B. The elongation of the second primer would displace the noninvading strand as shown in FIG. 8C. In this embodiment, as the target nucleic acid is amplified, the non-invading strand of primer 1 is displaced. If both primer one and primer two are partly double stranded primers, then the non-invading strands of both primer one and primer two will accumulate in solution as the target nucleic acid is amplified.

In one embodiment of the invention, at least two of the primers in a RPA reaction are partially double stranded and partially single stranded each generated by the hybridization of an invading strand and a non-invading oligonucleotide strand, which possess sequences of sufficiently complementary that they form a double stranded region. Preferably, the two oligonucleotide strands are sufficiently complementary over the relevant region that they can form a double stranded structure in RPA reaction conditions.

In an embodiment of the invention, the primers, including single-stranded and partially double-stranded primers, are labeled with a detectable label. It should be noted that a fluorescence quencher is also considered a detectable label. For example, the fluorescence quencher may be contacted to a fluorescent dye and the amount of quenching is detected. The detectable label should be such that it does not interfere with an elongation reaction. Where the primer is partially double stranded with an invading strand and a non-invading strand, the detectable label should be attached in such a way so it would not interfere with the elongation reaction of the invading strand. The non-invading strand of a partially double stranded primer is not elongated so there are no limitations on the labeling of the non-invading strand with the sole exception being that the label on the non-invading strand should not interfere with the elongation reaction of the invading strand. Labeled primers offer the advantage of a more rapid detection of amplified product. In addition, the detection of unincorporated label, that is, labeled oligonucleotides that have not been extended, will allow the monitoring of the status of the reaction.

Monitoring a RPA reaction may involve, for example, removing a fraction of an RPA reaction, isolating the unincorporated fraction, and detecting the unincorporated primer. Since the size of an unincorporated primer may be less than 50 bp, less than 40 bp, less than 30 bp or less than 25 bp, and the size of the amplified product may be greater than 1 Kb, greater than 2 Kb, greater than 5 Kb, or greater than 10 Kb, there is a great size difference between the incorporated and unincorporated primer. The isolation of the unincorporated primer may be performed rapidly using size exclusion chromatography such as, for example, a spin column. If a primer is labeled, a monitor procedure comprising a spin column and a measurement (e.g., fluorescence or radioactivity) can be performed in less than one minute. Another alternative for separating elongated primers from unelongated primers involve the use of PAGE. For example, the elongated primer may be separated from the unelongated primer by gel electrophoresis in less than 5 minutes. Yet another alternative for separating elongated primers involves the use of immobilized oligonucleotides. For example oligonucleotides homologous to sequences found uniquely within the amplified DNA sequence can be used to capture nucleic acids produced by primer elongation specifically. These capturing oligonucleotides immobilized on a chip, or other substrate. Capture of the elongated oligonucleotides by the capturing oligonucleotides can be performed by RecA protein mediated methods, or by traditional solution hybridizations if necessary.

In another embodiment of the invention, a double stranded primer may be labeled such that the separation of the two strands of the primer may be detected. As discussed above, after multiple rounds of elongation, the invading strand and the noninvading strands of a partially double stranded primer is separated. After this separation, the non-invading strand does not participate in the RPA reaction. This characteristic may be used to detect and monitor a RPA reaction in a number of ways.

In this application, the detectable label may be a fluorescent label or an enzyme and the label quencher (also referred to as the label inhibitor) may be a fluorescence quencher or an enzyme inhibitor. In these cases, the label is detected by fluorescence or enzyme inhibition. The delectability of the label would be the fluorescence if a fluorescent label is used or enzyme activity if an enzyme is used.

In the first method, the invading strand may be labeled with a label and the non-invading strand may be labeled with a detectable label quencher. The label, in the proximity of the label quencher (label inhibitor) on the partially double stranded primer would not be highly detectable. After RPA, the invading strand would be separated from the noninvading strand and thus, the label and the label quencher would be separated. The separation would cause the label to be more detectable. Thus, RPA reactions may be monitored by measuring the increases in the amount of detectable label.

The second method is similar to the first method except that the invading strand is modified with a label quencher while the noninvading strand is modified with a label. Then RPA is allowed to proceed with the result (same as method 1) of the label being separated from the label quencher. Thus, the overall delectability of the label would increase.

The third method involves labeling the noninvading strand of one double stranded primer with a label. In addition, the noninvading strand of a second double stranded primer is labeled with a label quencher. The two non-invading stands are designed to be complementary to each other. In this configuration, the RPA reaction is initially fluorescent. As the RPA reaction progresses, the two noninvading strands are displaced into solution and they hybridize to each other because they are designed to be complementary. As they hybridize, the label and the label quencher are brought into proximity to each other and the fluorescence of the reaction is decreased. The progress of the RPA reaction may be measured by monitoring the decrease in label detectability.

In a fourth method, the noninvading strands of a first and second double stranded primers are labeled with a first label and a second label. The two noninvading strands are also designed to be complementary to each other. As in the third method, after RPA, the two noninvading strands are hybridized to each other and the proximity of the two labels will be a reflection of the progress of the RPA reaction. The proximity of the two labels may be determined, for example, by direct observation or by isolation of the non-invading strands. As discussed above, isolation of primers and other small nucleic acids can be accomplished by size exclusion columns (including spin columns) or by gel electrophoresis.

In another embodiment of the invention, the non-invading strand of one or both of the primers is homologous to a second region of nucleic acid such that the primer can hybridize to and primer DNA synthesis at the second region of nucleic acid. Using this method, a second RPA reaction using the noninvading stand from the primer of a first RPA may be started. The product of the second RPA may be monitored to determine the progress of the first RPA.

In yet another embodiment of the invention, the non-invading strand is detected by a biosensor specific for the sequence of the non-invading strand. For example, the biosensor may be a surface with a nucleic acid sequence complementary to the non-invading strand. The biosensor may monitor a characteristic that results from the binding of the non-invading strand. The characteristic may be a detectable label.

Suitable detectable labels for any of the methods of the invention include enzymes, enzyme substrates, coenzymes, enzyme inhibitors, fluorescent markers, chromophores, luminescent markers, radioisotopes (including radionucleotides) and one member of a binding pair. More specific examples include fluorescein, phycobiliprotein, tetraethyl rhodamine, and beta-gal. Bind pairs may include biotin/avidin, biotin/strepavidin, antigen/antibody, ligand/receptor, and analogs and mutants of the binding pairs.

The recombinase agent of the invention may be RecA, RadA, RadB, Rad 51 or a functional analog or homologues of these proteins. If desired, the recombinase may be a temperature-sensitive (referred to herein as "ts") recombinase agent. If a ts recombinase is used, the RPA reaction may be started at one temperature (the permissive temperature) and terminated at another temperature (the non permissive temperature). Combinations of permissive temperatures may be, for example 25° C./30° C., 30° C./37° C., 37° C./42° C. and the like. In a preferred embodiment, the ts protein is reversible. A reversible ts protein's activity is restored when it is shifted from the nonpermissive temperature to the permissive temperature.

In a preferred embodiment, the RPA is performed in the presences of ATP, an ATP analog, or another nucleoside triphosphate. The ATP analog may be, for example, ATPγS, dATP, ddATP, or another nucleoside triphosphate analog such as UTP.

Other useful reagents that may be added to an RPA reaction include nucleotide triphosphates (i.e., dNTPs such as dATP, dTTP, dCTP, dGTP and derivatives and analogs thereof) and a DNA polymerase. Other useful reagents useful for leading/lagging RPA include NTPs (ATP, GTP, CTP, UTP and derivatives and analogs thereof). One advantage of the RPA reaction is that there is no limit on the type of polymerase used. For example, both eukaryotic and prokaryotic polymerases can be used. Prokaryotic polymerase include, at least, E. coli pol I, E. coli pol II, E. coli pol III, E. coli pol IV and E. coli polV. Eukaryotic polymerase include, for example, multiprotein polymerase complexes selected from the group consisting of pol-α, pol-β, pol-δ, and pol-ε.

In another embodiment of the invention, the RPA process is performed in the presence of an accessory component to improve polymerase processivity or fidelity. Both eukaryotic and prokaryotic accessory components may be used. Preferably, the accessory component is an accessory protein is from E. coli. Useful accessory proteins include single-strand binding protein, helicase, topoisomerase and resolvase. Other useful accessory proteins include a sliding clamp selected from the group consisting of an E. coli β-dimer sliding clamp, an eukaryotic PCNA sliding clamp and a T4 sliding clamp gp45. Other accessory components include a DNA Polymerase III holoenzyme complex consisting of β-Clamp, DnaX Clamp Loader, and the Polymerase Core Complex. Still other accessory component include RuvA, RuvB, RuvC and RecG. The properties endowed by the use of additional components will likely enable the amplification of large DNAs not previously successfully targeted by current methods such as PCR.

In another embodiment, the RPA is performed in the presence of agents used to stabilize a RecA/ssDNA nucleoprotein filaments. For example, the agent may be RecR, RecO, RecF or a combination of these proteins. Other useful agents include PriA, PriB, DnaT, DnaB, DnaC, and DnaG.

One benefit of the present invention is that the RPA reaction may be performed at reduced temperatures compared to a PCR reaction. For example, the RPA process may be performed between 20° C. and 50° C. Preferably, the RPA process is performed at less than 45° C. More preferably, the RPA process may be performed at less than 40° C. Even more preferably, the RPA process may be performed at less than 35° C. Most preferably, the RPA process may be performed at less than 30° C. One of the reasons that the RPA process can be performed at these reduced temperatures is because RPA may be performed without temperature induced melting of the template nucleic acid. Further, unlike PCR, absolute temperature control is not required and the temperature can fluctuate without adversely affecting RPA. For example, the amount of fluctuation may be anywhere within the temperatures specified above. The temperature necessary for melting of double stranded DNA also contribute to premature enzyme inactivation, a disadvantage absent in the methods of this invention.

RPA may be performed to test for the presences or absences of a genotype. The genotype tested may be associated with a disease or a predisposition to a disease. Alternatively, the genotype may be associated with a normal phenotype or a phenotype that confers special resistance to a disease. The genotype as disclosed above may be any standard genetic variant such as a point mutation, a deletion, an insertion, an inversion, a frameshift mutation, a crossover event, or the presence or absences of multiple copies of a genetic sequence (e.g., the presences of minichromosomes).

One method of detecting a genotype is to detect the distance between a primer pair in an RPA reaction. The distance between a primer pair is reflected by the size of the amplified sequence. In that method, the two primers are selected such that it spans a target region such as, for example, a gene. Then RPA is performed using the primer pair and the RPA product is analyzed. The analysis may involve determining the size or sequence of the amplified product. Methods of determining the size of a DNA sequence, including at least techniques such as agarose gels, PAGE gels, mass spectroscopy, pulsed field gels, gene chips, sucrose sedimentation and the like are known. There are many DNA sequencing methods and their variants, such as the Sanger sequencing using dideoxy termination and denaturing gel electrophoresis (Sanger, F., Nichlen, S. & Coulson, A. R. Proc. Natl. Acad. Sci. U.S.A. 75, 5463-5467 (1977)), Maxam-Gilber sequencing using chemical cleavage and denaturing gel electrophoresis (Maxam, A. M. & Gilbert, W. Proc Natl Acad Sci USA 74, 560-564 (1977)), pyro-sequencing detection pyrophosphate (PPi) released during the DNA polymerase reaction (Ronaghi, M., Uhlen, M. & Nyren, P. Science 281, 363, 365 (1998)), and sequencing by hybridization (SBH) using oligonucleotides (Lysov, I., Florent'ev, V. L., Khorlin, A. A., Khrapko, K. R. & Shik, V. V. Dokl Akad Nauk SSSR 303, 1508-1511 (1988); Bains W. & Smith G. C. J. Theor. Biol 135, 303-307(1988); Drnanac, R., Labat, I., Brukner, I. & Crkvenjakov, R. Genomics 4, 114-128 (1989); Khrapko, K. R., Lysov, Y., Khorlyn, A. A., Shick, V. V., Florentiev, V. L. & Mirzabekov, A. D. FEBS Lett 256. 118-122 (1989); Pevzner P. A. J Biomol Struct Dyn 7, 63-73 (1989); Southern, E. M., Maskos, U. & Elder, J. K. Genomics 13, 1008-1017 (1992)).

One method of detecting a genotype is to use primers that are specific for a particular genotype. For example, a primer may be designed to efficiently amplified one genotype but inefficiently or not amplify another genotype at all. In an embodiment, the primer may comprise a 3' sequence that is complementary to one genotype (e.g., a genetic disease genotype) but not to another genotype (e.g., a normal genotype).

The genotype to be determined may be indicative of a disease such as, for example, the presence of an activated oncogene; the presence of the gene for Huntington's disease or the absence of an anti-oncogene.

The 3' bases of the primers are especially important in determining the specificity and efficiency of an RPA reaction. A primer may be designed so that the 3' base is complementary to one genotype and not complementary to another genotype. This will allow efficient RPA of one genotype and an inefficient RPA (if any) of the second genotype. It is noted that the method is effective if only one primer of the primer pair can differentiate between different phenotypes (by having different efficiencies of amplification). In a preferred embodiment, both primers in an RPA reaction can differentiate between different genotypes. In this above example, the primers are complementary to one genotype and are not complementary to a second genotype by one base at its 3' end. In a preferred embodiment, the primer is not complementary to the second genotype by at least one base at its 3' end. Preferably, the primer is not complementary to the second genotype by at least 2, 3, 4, 5, 6, 7, 8, 9, or 10 bases at its 3' end. Most preferably, the primer is completely non-complementary or cannot hybridize to the second genotype while it can hybridize to said first genotype.

In some of the methods discussed, the presence or absence of an amplified product provides the indication of the presence or absence of a genotype. In these cases, the RPA reaction may be monitored by the methods discussed throughout the specification.

In a preferred embodiment, an RPA reaction for genotyping will amplify a sequence regardless of the genotype of the patient. However, the genotype of a patient will alter a characteristic of the amplified sequence. For example, the amplified sequence may be a different size, or sequence for one genotype than for another genotype. In that way, the RPA reaction will contain an internal control to indicate that the amplification reaction was performed successfully. Naturally, a method of RPA, which includes one or more additional pairs of primers as controls for the performance of the RPA reaction, is also envisioned.

In another embodiment, an RPA reaction may be used to determine the presence or absences of a nucleic acid molecule. The nucleic acid molecule may be from any organism. For example, the microbial composition of a sample may be determined by using a battery of RPA reactions directed to the nucleic acid of different microbes. RPA is especially useful for the detection of microbes. In one embodiment, the pathogens are selected from viruses, bacteria, parasites, and fungi. In further embodiments, the pathogens are viruses selected from influenza, rubella, varicella-zoster, hepatitis A, hepatitis B, other hepatitis viruses, herpes simplex, polio, smallpox, human immunodeficiency virus, vaccinia, rabies, Epstein Barr, retroviruses, and rhinoviruses. In another embodiment, the pathogens are bacteria selected from *Escherichia coli, Mycobacterium tuberculosis, Salmonella, Chlamydia* and *Streptococcus*. In yet a further embodiment, the pathogens are parasites selected from *Plasmodium, Trypanosoma, Toxoplasma gondii*, and *Onchocerca*. However, it is not intended that the present invention be limited to the specific genera and/or species listed above.

REFERENCES

Adams, D. E., Tsaneva, I. R. and West, S. C. (1994). Dissociation of RecA filaments from duplex DNA by the RuvA and RuvB DNA repair proteins. Proc Natl Acad Sci USA 91, 9901-5.

Alexseyev, A. A., Bakhlanova, I. V., Zaitsev, E. N. and Lanzov, V. A. (1996). Genetic characteristics of new RecA mutants of *Escherichia coli* K-12. J Bacteriol 178, 2018-24.

Baumann, P., Benson, F. E., Hajibagheri, N. and West, S. C. (1997). Purification of human Rad51 protein by selective spermidine precipitation. Mutat Res 384, 65-72.

Benkovic, S. J., Valentine, A. M. and Salinas, F. (2001). Replisome-mediated DNA replication. Annu Rev Biochem 70, 181-208.

Bennett, R. L. and Holloman, W. K. (2001). A RecA homologue in *Ustilago maydis* that is distinct and evolutionarily distant from Rad51 actively promotes DNA pairing reactions in the absence of auxiliary factors. Biochemistry 40, 2942-53.

Better, M. and Helinski, D. R. (1983). Isolation and characterization of the RecA gene of *Rhizobium meliloti*. J Bacteriol 155, 311-6.

Bork, J. M., Cox, M. M. and Inman, R. B. (2001). The RecOR proteins modulate RecA protein function at 5' ends of single-stranded DNA. Embo J 20, 7313-22.

Cox, M. M., Goodman, M. F., Kreuzer, K. N., Sherratt, D. J., Sandler, S. J. and Marians, K. J. (2000). The importance of repairing stalled replication forks. Nature 404, 37-41.

Cox, M. M., McEntee, K. and Lehman, I. R. (1981). A simple and rapid procedure for the large scale purification of the RecA protein of *Escherichia coli*. J Biol Chem 256, 4676-8.

Cromie, G. A. and Leach, D. R. (2000). Control of crossing over. Mol Cell 6, 815-26.

Dillingham, M. S. and Kowalczykowski, S. C. (2001). A step backward in advancing DNA replication: rescue of stalled replication forks by RecG. Mol Cell 8, 734-6.

Eggleston, A. K. and West, S. C. (2000). Cleavage of holliday junctions by the *Escherichia coli* RuvABC complex. J Biol Chem 275, 26467-76.

Glover, B. P. and McHenry, C. S. (2001). The DNA polymerase III holoenzyme: an asymmetric dimeric replicative complex with leading and lagging strand polymerases. Cell 105, 925-34.

Goodman, H. J., Parker, J. R., Southern, J. A. and Woods, D. R. (1987). Cloning and expression in *Escherichia coli* of a RecA-like gene from *Bacteroides fragilis*. Gene 58, 265-71.

Heyer, W. D. and Kolodner, R. D. (1989). Purification and characterization of a protein from *Saccharomyces cerevisiae* that binds tightly to single-stranded DNA and stimulates a cognate strand exchange protein. Biochemistry 28, 2856-62.

Hickson, I. D., Gordon, R. L., Tomkinson, A. E. and Emmerson, P. T. (1981). A temperature sensitive Reca protein of *Escherichia coli*. Mol Gen Genet. 184, 68-72.

Hsieh, P., Camerini-Otero, C. S. and Camerini-Otero, R. D. (1992). The synapsis event in the homologous pairing of DNAs: RecA recognizes and pairs less than one helical repeat of DNA. Proc Natl Acad Sci USA 89, 6492-6.

Kato, R. and Kuramitsu, S. (1993). RecA protein from an extremely thermophilic bacterium, *Thermus thermophilus* HB8. J Biochem (Tokyo) 114, 926-9.

Kelman, Z. and O'Donnell, M. (1995). DNA polymerase III holoenzyme: structure and function of a chromosomal replicating machine. Annu Rev Biochem 64, 171-200.

Komori, K., Miyata, T., DiRuggiero, J., Holley-Shanks, R., Hayashi, I., Cann, I. K., Mayanagi, K., Shinagawa, H. and Ishino, Y. (2000). Both RadA and RadB are involved in homologous recombination in *Pyrococcus furiosus*. J Biol Chem 275, 33782-90.

Kornberg, A. and Baker, T. A. (1992). DNA Replication. New York: W. H. Freeman and Company.

Kuramitsu, S., Hamaguchi, K., Ogawa, T. and Ogawa, H. (1981). A large-scale preparation and some physicochemical properties of RecA protein. J Biochem (Tokyo) 90, 1033-45.

Kurumizaka, H., Ikawa, S., Ikeya, T., Ogawa, T. and Shibata, T. (1994). A chimeric RecA protein exhibits altered double-stranded DNA binding. J Biol Chem 269, 3068-75.

Liu, J., Nurse, P. and Marians, K. J. (1996). The ordered assembly of the phiX174-type primosome. III. PriB facilitates complex formation between PriA and DnaT. J Biol Chem 271, 15656-61.

Lovett, C. M., Jr. and Roberts, J. W. (1985). Purification of a RecA protein analogue from *Bacillus subtilis*. J Biol Chem 260, 3305-13.

Maeshima, K., Morimatsu, K. and Horii, T. (1996). Purification and characterization of XRad51.1 protein, *Xenopus* RAD51 homologue: recombinant XRad51.1 promotes strand exchange reaction. Genes Cells 1, 1057-68.

Marians, K. J. (1992). Prokaryotic DNA replication. Annu Rev Biochem 61, 673-719.

Marians, K. J. (1999). PriA: at the crossroads of DNA replication and recombination. Prog Nucleic Acid Res Mol Biol 63, 39-67.

Mazin, A. V. and Kowalczykowski, S. C. (1998). The function of the secondary DNA-binding site of RecA protein during DNA strand exchange. Embo J 17, 1161-8.

McGlynn, P. and Lloyd, R. G. (1999). RecG helicase activity at three- and four-strand DNA structures. Nucleic Acids Res 27, 3049-56.

McGlynn, P., Mahdi, A. A. and Lloyd, R. G. (2000). Characterisation of the catalytically active form of RecG helicase. Nucleic Acids Res 28, 2324-32.

Morel, P., Chemy, D., Ehrlich, S. D. and Cassuto, E. (1997). Recombination-dependent repair of DNA double-strand breaks with purified proteins from *Escherichia coli*. J Biol Chem 272, 17091-6.

Ng, J. Y. and Marians, K. J. (1996a). The ordered assembly of the phiX174-type primosome. I. Isolation and identification of intermediate protein-DNA complexes. J Biol Chem 271, 15642-8.

Ng, J. Y. and Marians, K. J. (1996b). The ordered assembly of the phiX174-type primosome. II. Preservation of primosome composition from assembly through replication. J Biol Chem 271, 15649-55.

Paulus, B. F. and Bryant, F. R. (1997). Time-dependent inhibition of RecA protein-catalyzed ATP hydrolysis by ATP-gammaS: evidence for a rate-determining isomerization of the RecA-ssDNA complex. Biochemistry 36, 7832-8.

Pham, P., Bertram, J. G., O'Donnell, M., Woodgate, R. and Goodman, M. F. (2001). A model for SOS-lesion-targeted mutations in *Escherichia coli*. Nature 409, 366-70.

Pierre, A. and Paoletti, C. (1983). Purification and characterization of RecA protein from *salmonella typhimurium*. J Biol Chem 258, 2870-4.

Rashid, N., Morikawa, M., Kanaya, S., Atomi, H. and Imanaka, T. (2001). RecA/Rad51 homolog from *Thermococcus kodakaraensis* KODI. Methods Enzymol 334, 261-70.

Rosselli, W. and Stasiak, A. (1990). Energetics of RecA-mediated recombination reactions. Without ATP hydrolysis RecA can mediate polar strand exchange but is unable to recycle. J Mol Biol 216, 335-52.

Shan, Q., Bork, J. M., Webb, B. L., Inman, R. B. and Cox, M. M. (1997). RecA protein filaments: end-dependent dissociation from ssDNA and stabilization by RecO and RecR proteins. J Mol Biol 265, 519-40.

Singleton, M. R., Scaife, S. and Wigley, D. B. (2001). Structural analysis of DNA replication fork reversal by RecG. Cell 107, 79-89.

Spies, M., Kil, Y., Masui, R., Kato, R., Kujo, C., Ohshima, T., Kuramitsu, S. and Lanzov, V. (2000). The RadA protein from a hyperthermophilic archaeon *Pyrobaculum islandicum* is a DNA-dependent ATPase that exhibits two disparate catalytic modes, with a transition temperature at 75 degrees C. Eur J Biochem 267, 1125-37.

Steffen, S. E. and Bryant, F. R. (2000). Purification and characterization of the RecA protein from *Streptococcus pneumoniae*. Arch Biochem Biophys 382, 303-9.

Tang, M., Pham, P., Shen, X., Taylor, J. S., O'Donnell, M., Woodgate, R. and Goodman, M. F. (2000). Roles of *E. coli* DNA polymerases IV and V in lesion-targeted and untargeted SOS mutagenesis. Nature 404, 1014-8.

Tissier, A. F., Lopez, M. F. and Signer, E. R. (1995). Purification and characterization of a DNA strand transferase from broccoli. Plant Physiol 108, 379-86.

Webb, B. L., Cox, M. M. and Inman, R. B. (1995). An interaction between the *Escherichia coli* RecF and RecR proteins dependent on ATP and double-stranded DNA. J Biol Chem 270, 31397-404.

Webb, B. L., Cox, M. M. and Inman, R. B. (1997). Recombinational DNA repair: the RecF and RecR proteins limit the extension of RecA filaments beyond single-strand DNA gaps. Cell 91, 347-56.

Webb, B. L., Cox, M. M. and Inman, R. B. (1999). ATP hydrolysis and DNA binding by the *Escherichia coli* RecF protein. J Biol Chem 274, 15367-74.

West, S. C., Countryman, J. K. and Howard-Flanders, P. (1983). Purification and properties of the RecA protein of *Proteus mirabilis*. Comparison with *Escherichia coli* RecA protein; specificity of interaction with single strand binding protein. J Biol Chem 258, 4648-54.

Wetmur, J. G., Wong, D. M., Ortiz, B., Tong, J., Reichert, F. and Gelfand, D. H. (1994). Cloning, sequencing, and expression of RecA proteins from three distantly related thermophilic eubacteria. J Biol Chem 269, 25928-35.

EXAMPLES

Example 1

Leading Strand Recombinase-Polymerase Amplification (lsRPA)

Figure 1:
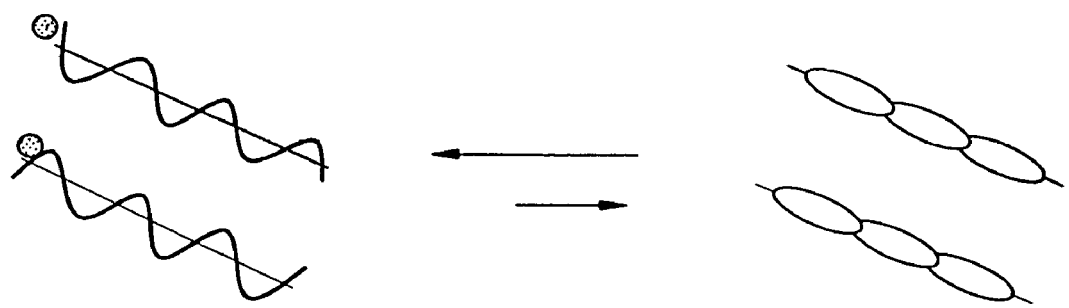
FIG. 1 depicts a schematic representation of RecA/Primer Loading.

DNA sequences can be amplified using leading strand synthesis according to the Recombinase-Polymerase amplification (RPA) method depicted in FIG. 1.

A reaction is assembled with the following composition:

D-Loop Formation/Resolution Components

| Component | Concentration |
| --- | --- |
| RecA | 20 µM |
| Single-stranded oligonucleotide primers | 0.25 µM |
| ATP | 3 mM |
| RecF | 0.1 µM |
| RecO | 0.13 µM |
| RecR | 0.5 µM |
| Single-stranded Binding protein (SSB) | 1 to 10 µM |
| DNA polymerase V | 5 units |

Polymerase/Helicase/Resolvase Mix

| Component | Concentration |
| --- | --- |
| DNA Polymerase | 5 units |
| RuvA | 0.5 µM |
| RuvB | 0.5 µM |
| RuvC | 0.5 µM |
| RecG | 10 nM |

Reaction Buffer

| Component | Concentration |
| --- | --- |
| MgCl2 | 2 to 10 mM |
| TrisHCl pH 7.2 | 10 mM |
| DTT | 0 to 10 mM |
| KCl | 0 to 50 mM |
| Deoxyribonucleotide triphosphates | 0.2 mM |
| Bovine serum albumin (BSA) | 0 to 10 µg per ml |

The reaction is assembled so that the final concentration satisfies the D-Loop Formation/Resolution Components, Polymerase/Helicase/Resolvase Mix, and Reaction Buffer with the DNA polymerase and/or template added last if necessary. For example, a 2× concentrated solution of D-Loop Formation/Resolution Components and of the Polymerase/Helicase/Resolvase Mix may be made in 1× reaction buffer. The reaction may be initiated by mixing an equal volume of each of the two components (each in 1× reaction buffer). Optionally, and as stated above, the DNA polymerase or template (target DNA) may be added last. The reaction is incubated for a sufficient time of until the reactants are exhausted. Typical incubation times would range from 1 hour, 2 hours, 3 hours, 5 hours, 10 hours or overnight (about 16 hours). Unlike PCR, which requires small volumes for rapid temperature change, there is no limit to the reaction volume of RPA. Reaction volumes of 25 ul, 50 ul, 100 ul, 1 ml, 10 ml and 100 ml or larger may be performed in one vessel. Incubation temperature may be typical laboratory temperatures such as 25° C., 30° C. or 37° C.

Prior to the addition of template DNA and/or Polymerase, RecA and SSB will compete for binding to single-stranded oligonucleotide primers. In the presence of a RecR and RecO, RecA is selectively stabilized onto the single-stranded primers forming RecA nucleoprotein filaments in a complex with RecO and RecR. This complex is competent to invade double-stranded DNA to form a D-loop at sites homologous to the oligonucleotide primers. Alternatively, RecA, RecO and RecR can be pre-loaded onto oligonucleotide primers prior to the introduction of SSB to the reaction mixture (FIG. 1). The invading strands will be extended by the polymerase in a 5' to 3' direction. As D-loops are formed and synthesis proceeds displaced single stranded DNA becomes coated with SSB. RecA release from double-stranded DNA can occur via ATP hydrolysis in a 5' to 3' direction or as a result of helicase/resolvase or polymerase activity (FIGS. 2A, B). New rounds of invasion/synthesis will continuously occur. The third round of strand-invasion/synthesis will release discrete products released whose ends correspond to the two facing primer sites. These fragments will soon become the dominant reaction product and will accumulate to high levels. As each synthetic complex processes to the end of the template RecA protein is displaced either by polymerase activity or by the activity of helicases, such as RuvAB or resolvases, such as RuvC. Once primers, ATP, deoxynucleoside triphosphates, or any other limiting component is exhausted, the reaction will stop.

The inclusion of temperature-sensitive RecA mutants will allow the controlled initiation of DNA synthesis. In such a situation, the initiation reaction is performed at 25 to 37° C. permitting the formation of D-loops. Elongation reactions are performed at 42° C., which is non-permissive for RecA mediated double-strand invasion. The number of cycles will determine the amount of reaction product. Extended elongation phases will permit the amplification of extremely long DNAs without interference of re-invasion.

Example 2

Nested RPA

The RPA reaction is performed as described in Example 1. A fraction of one tenth (1/10) and one hundredth (1/100) of the reaction is removed and used in place of the DNA template in a second round of RPA. lsRPA, leading/lagging RPA, and combinations thereof may be used for nested RPA.

Example 3

Simultaneous Leading And Lagging Strand Recombinase-Polymerase Amplification DNA sequences can be amplified using simultaneous leading and lagging strand synthesis according to the Recombinase-Polymerase amplification (RPA) method depicted in FIG. 2.

A reaction is assembled with the following composition:

D-Loop Formation/Resolution Components

| Component | Concentration |
| --- | --- |
| RecA | 20 µM |
| Single-stranded oligonucleotide primers | 0.25 µM |
| ATP | 3 mM |
| RecF | 0.1 µM |
| RecO | 0.13 µM |
| RecR | 0.5 µM |
| Single-stranded Binding protein (SSB) | 1 to 10 µM |
| DNA polymerase V | 5 units |

Helicase/Resolvase Mix

| Component | Concentration |
| --- | --- |
| RuvA | 0.5 µM |
| RuvB | 0.5 µM |
| RuvC | 0.5 µM |
| RecG | 10 nM |

Primosome Complex

| Component | Concentration |
| --- | --- |
| PriA | 20 nM |
| PriB | 20 nM |
| DnaT | 100 nM |
| DnaB | 100 nM |
| DnaC | 200 nM |
| DnaG | 200 nM |

Text

DNA Polymerase III Holoenzyme Complex

| Component | Concentration |
| --- | --- |
| β-Clamp | 2 μM |
| DnaX Clamp Loader | 500 nM |
| Polymerase Core Complex | 500 nM |

Lagging Strand Mix

| Component | Concentration |
| --- | --- |
| DNA polymerase I | 5 units |
| DNA ligase | 2 units |

Reaction Buffer

| Component | Concentration |
| --- | --- |
| $MgCl_2$ | 2 to 10 mM |
| TrisHCl pH 7.2 | 10 to 20 mM |
| DTT | 0 to 10 mM |
| KCl | 0 to 50 mM |
| Deoxyribonucleotide triphosphates | 0.2 to 0.4 mM |
| Bovine serum albumin (BSA) | 0 to 10 μg per ml |

The reaction is assembled so that the final concentration of all the reagents is as listed above. Thus, for example, a 5 fold concentrated solution of each of the components (D-loop Formation/Resolution Components, Helicase/Resolvase Mix, Primosome Complex, DNA Polymerase III holoenzyme Complex, Lagging Strand Mix) is made in 1× reaction buffer. Then, the five solutions are mixed together in equal volumes to initiate the reaction. The reaction is incubated for a sufficient time of until the reactants are exhausted. Typical incubation times would range from 1 hour, 2 hours, 3 hours, 5 hours, 10 hours or overnight (about 16 hours). As stated above, there is no limit to the reaction volume of RPA. Reaction volumes of 25 ul, 50 ul, 100 ul, 1 ml, 10 ml and 100 ml or larger may be performed in one vessel. Incubation temperature may be typical laboratory temperatures such as 25° C., 30° C. or 37° C.

First, the primosome loads onto the D-loop formed by RecA nucleoprotein filament invasion. The primosome synthesizes a stretch of RNA primer. Finally, primosome recruits the clamp loader, which recruits both the sliding clamp dimer and the asymmetric DNA polymerase core (FIG. 3A).

Synthesis occurs simultaneously in both the leading and lagging directions. Eventually lagging strand synthesis stops and the lagging strand clamp is unloaded. Synthesis of the leading strand continues until a new site of lagging stand synthesis is formed (FIG. 3B).

While leading strand synthesis continues, a new site of lagging stand synthesis is formed. Lagging strand synthesis continues back to the previous Okazaki fragment where the lagging strand clamp is unloaded (FIG. 3C).

DNA Polymerase I removes the RNA primer, and fills in the gap while DNA ligase connects the two Okazaki fragments forming a continuous lagging strand (FIG. 3D).

We claim:

1. A method of recombinase-polymerase amplification of a double-stranded target sequence polymer molecule, comprising:
   (a) contacting a recombinase agent with a first primer sequence molecule to form a first recombinase agent-primer pair and contacting a recombinase agent with a second primer sequence molecule to form a second recombinase agent-primer pair;
   (b) contacting the first and second recombinase agent-primer pairs with the double-stranded target sequence polymer molecule to form a structure, wherein the first and second primer sequence molecules of the recombinase agent-primer pairs associate with the double-stranded target sequence polymer molecule;
   (c) extending the first and second primer sequence molecules along the double-stranded target sequence polymer molecule with a polymerase molecule and monomers to be incorporated into the extended first and second primer sequence molecules, using the double-stranded target sequence polymer molecule as a template;
   (d) contacting the double-stranded target sequence polymer molecule with primosome assembly proteins, a clamp loader/polymerase III holoenzyme complex, a DNA polymerase III core, a DNA polymerase I, a primase, a helicase, and a ligase;
   (e) replicating the strand of the double-stranded target sequence polymer molecule that is displaced by the recombinase agent-primer pair structures through lagging strand synthesis; and
   (f) repeating steps (b) through (e) until a desired degree of amplification is achieved.

2. The method of claim 1, further comprising:
   (a) contacting one or more additional primer sequence molecules with a recombinase agent to form one or more recombinase agent-primer pairs;
   (b) contacting the one or more additional recombinase agent-primer pairs with the target sequence polymer molecule or extended primer sequence molecule;
   (c) extending the one or more additional primer sequence molecules along the target sequence polymer molecule or extended primer sequence molecule with a polymerase molecule and monomers to be incorporated into the one or more extended primer sequence molecules, using the target sequence polymer molecule or extended primer sequence molecule as a template, wherein the extended one or more additional primer sequence is contained within the first or second extended primer sequence; and
   (d) repeating steps (b) and (c) until a desired degree of amplification is achieved.

3. The method of claim 1, wherein the target sequence polymer molecule is non-natural.

4. The method of claim 1, wherein the target sequence molecule is DNA or RNA.

5. The method of claim 1, wherein one or more primer sequence molecules is associated with a detectable label.

6. The method of claim 1, further comprising the presence of RecF, RecG, RecO, RecT, RuvA, RuvB, or SSB during extension.

7. The method of claim 1, wherein the recombinase agent is RecA.

8. A recombinase-polymerase amplification mixture of substantially purified components, comprising a target sequence polymer molecule, a recombinase agent, a primer sequence molecule, a polymerase molecule, primosome assembly proteins, a clamp loader/polymerase III holoenzyme complex, a DNA polymerase III core, a DNA polymerase I, a primase, a helicase, and a ligase.

9. The mixture of claim 8, wherein the target sequence molecule is DNA or RNA.

10. The mixture of claim 8, wherein a primer sequence molecule is associated with a detectable label.

11. The mixture of claim 8, further comprising the presence of RecF, RecG, RecO, RecT, RuvA, RuvB, or SSB.

12. The mixture of claim 8, wherein the recombinase agent is RecA.

* * * * *